(12) United States Patent
De Kock et al.

(10) Patent No.: US 10,888,697 B2
(45) Date of Patent: Jan. 12, 2021

(54) FIXATION MECHANISM FOR AN IMPLANTABLE LEAD

(71) Applicant: CARDIAC PACEMAKERS, INC., St. Paul, MN (US)

(72) Inventors: Andrew L. De Kock, Ham Lake, MN (US); G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 229 days.

(21) Appl. No.: 16/104,262

(22) Filed: Aug. 17, 2018

(65) Prior Publication Data

US 2019/0054290 A1  Feb. 21, 2019

Related U.S. Application Data

(60) Provisional application No. 62/547,187, filed on Aug. 18, 2017.

(51) Int. Cl.
| | | |
|---|---|---|
| *A61N 1/05* | (2006.01) | |
| *A61N 1/375* | (2006.01) | |
| *A61B 17/34* | (2006.01) | |
| *A61B 17/32* | (2006.01) | |

(52) U.S. Cl.
CPC .......... *A61N 1/057* (2013.01); *A61N 1/0504* (2013.01); *A61N 1/3752* (2013.01); *A61B 17/3468* (2013.01); *A61B 2017/320056* (2013.01); *A61N 1/0558* (2013.01); *A61N 2001/058* (2013.01)

(58) Field of Classification Search
CPC .... A61N 1/057; A61N 1/0504; A61N 1/3752; A61N 1/0558; A61N 2001/058; A61B 17/3468; A61B 2017/320056
See application file for complete search history.

(56) References Cited

U.S. PATENT DOCUMENTS

| | | |
|---|---|---|
| 4,716,888 A | 1/1988 | Wesner |
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,194,302 B2 | 3/2007 | Bardy et al. |
| 7,493,175 B2 | 2/2009 | Cates et al. |
| 7,655,014 B2 | 2/2010 | Ko et al. |
| 8,019,443 B2 | 9/2011 | Schleicher et al. |
| 8,244,377 B1 | 8/2012 | Pianca et al. |
| 8,285,397 B2 | 10/2012 | Grandhe |
| 8,332,043 B1 | 12/2012 | Jaax et al. |

(Continued)

FOREIGN PATENT DOCUMENTS

| | | |
|---|---|---|
| EP | 0085967 A1 | 8/1983 |
| WO | 2012151356 A1 | 11/2012 |

OTHER PUBLICATIONS

Search Report and Written Opinion dated Sep. 18, 2019 for International Application No. PCT/US2019/028506.

(Continued)

*Primary Examiner* — Erich G Herbermann
(74) *Attorney, Agent, or Firm* — Seager, Tufte & Wickhem LLP

(57) ABSTRACT

Tools adapted to allow a fixation device to be applied near the distal end of an implantable lead, and methods for using such tools. Preparing the lead for implantation may be performed by placing a tool over a distal tip of the lead, moving a fixation device from the tool to the lead, and placing the fixation device the lead.

10 Claims, 27 Drawing Sheets

(56) References Cited

U.S. PATENT DOCUMENTS

| | | |
|---|---|---|
| 9,610,435 B2 | 4/2017 | Schleicher et al. |
| 9,981,121 B2 | 5/2018 | Seifert et al. |
| 2004/0230279 A1 | 11/2004 | Cates et al. |
| 2004/0230282 A1 | 11/2004 | Cates et al. |
| 2007/0255295 A1 | 11/2007 | Starkebaum et al. |
| 2008/0208247 A1 | 8/2008 | Rutten et al. |
| 2009/0125059 A1 | 5/2009 | Verzal et al. |
| 2009/0210043 A1 | 8/2009 | Reddy |
| 2010/0131036 A1 | 5/2010 | Geistert et al. |
| 2010/0256696 A1 | 10/2010 | Schleicher et al. |
| 2011/0054580 A1 | 3/2011 | Desai et al. |
| 2011/0054581 A1 | 3/2011 | Desai et al. |
| 2013/0131767 A1 | 5/2013 | Desai et al. |
| 2014/0144580 A1 | 5/2014 | Desai et al. |
| 2014/0194963 A1 | 7/2014 | Desai et al. |
| 2014/0330248 A1 | 11/2014 | Thompson-Nauman et al. |
| 2014/0330327 A1 | 11/2014 | Thompson-Nauman et al. |
| 2015/0343199 A1 | 12/2015 | Wechter et al. |
| 2015/0352352 A1 | 12/2015 | Soltis et al. |
| 2016/0143643 A1 | 5/2016 | Smith et al. |
| 2016/0339233 A1 | 11/2016 | De Kock et al. |
| 2017/0020551 A1 | 1/2017 | Reddy et al. |
| 2017/0021159 A1 | 1/2017 | Reddy et al. |
| 2017/0095657 A1 | 4/2017 | Reddy et al. |
| 2017/0319845 A1 | 11/2017 | De Kock et al. |
| 2017/0319864 A1 | 11/2017 | De Kock et al. |
| 2018/0036527 A1 | 2/2018 | Reddy et al. |
| 2018/0036547 A1 | 2/2018 | Reddy |
| 2018/0078252 A1 | 3/2018 | Sato |
| 2018/0133458 A1 | 5/2018 | Foster et al. |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0193060 A1 | 7/2018 | Reddy et al. |
| 2018/0214686 A1 | 8/2018 | De Kock et al. |
| 2018/0296824 A1 | 10/2018 | De Kock et al. |
| 2018/0344200 A1 | 12/2018 | Thakur et al. |
| 2018/0344252 A1 | 12/2018 | An et al. |
| 2019/0054289 A1 | 2/2019 | Reddy et al. |
| 2019/0054290 A1 | 2/2019 | De Kock et al. |
| 2019/0117959 A1 | 4/2019 | Reddy |
| 2019/0151651 A1 | 5/2019 | Reddy et al. |

OTHER PUBLICATIONS

International Search Report and Written Opinion dated Oct. 29, 2019 for International Application No. PCT/US2019/042995.

Darrat et al; "Single Incision Technique for Placement of Subcutaneous Implantable Cardioverter Defibrillators," http://abstractsonline.com/pp8/, accessed May 14, 2018.

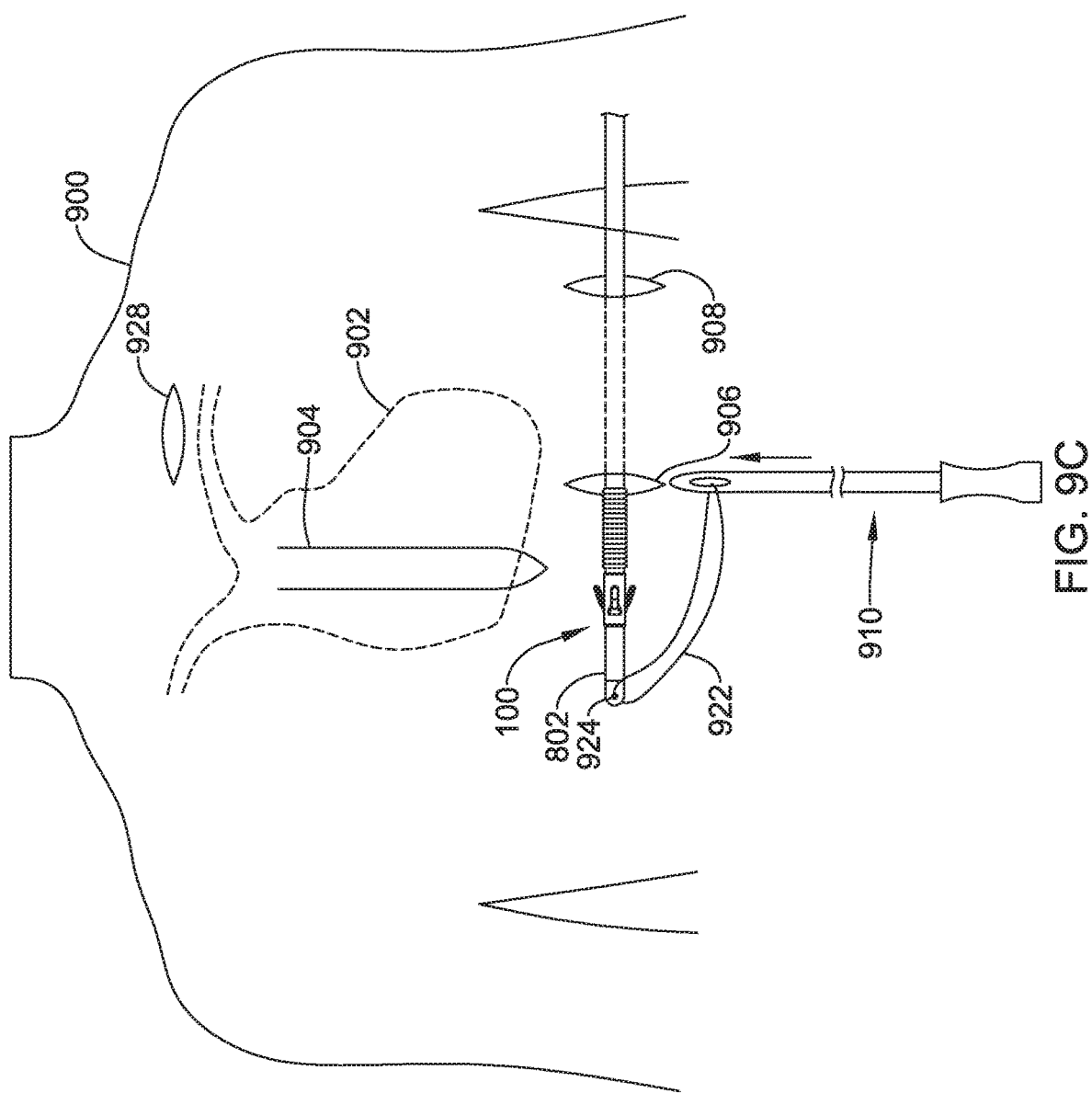

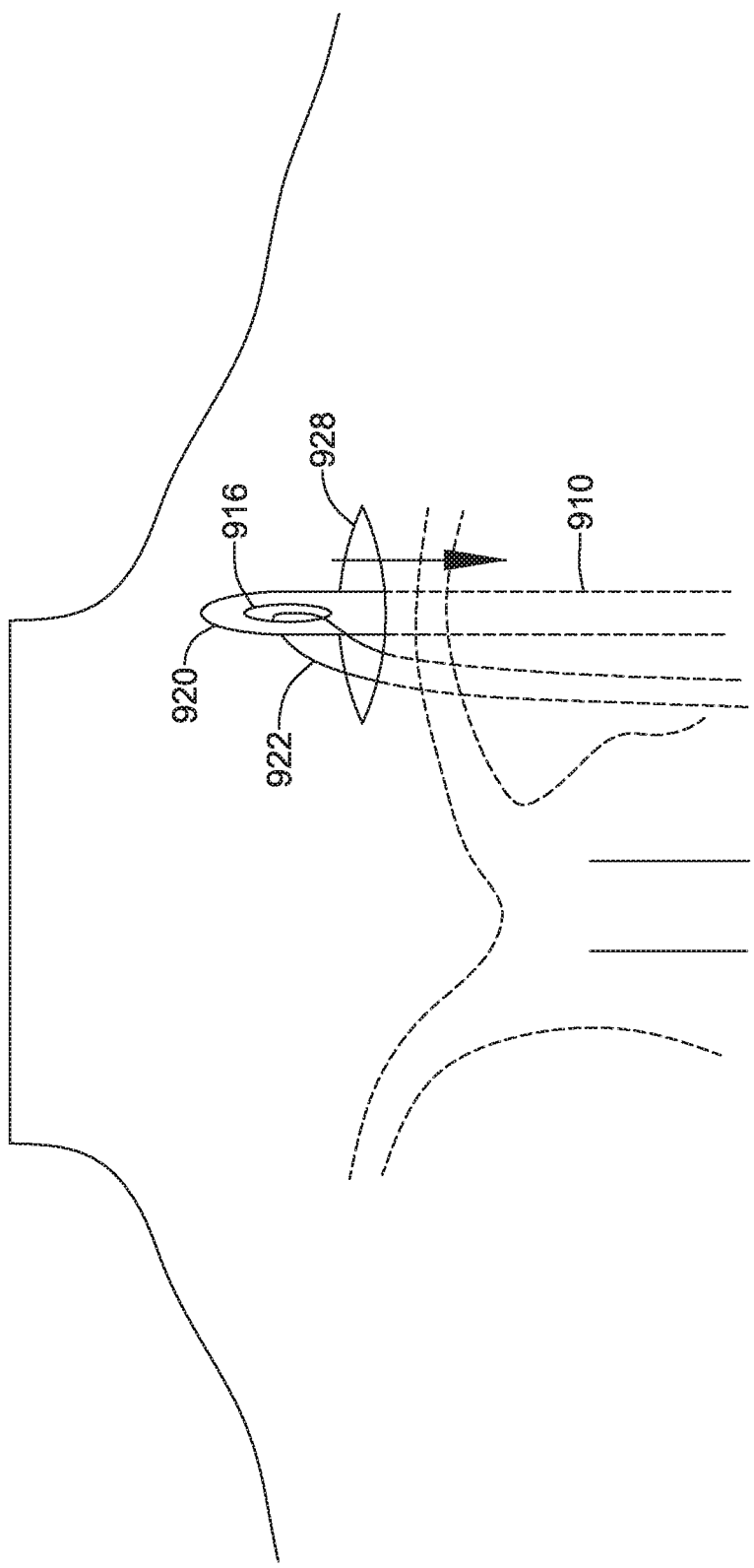

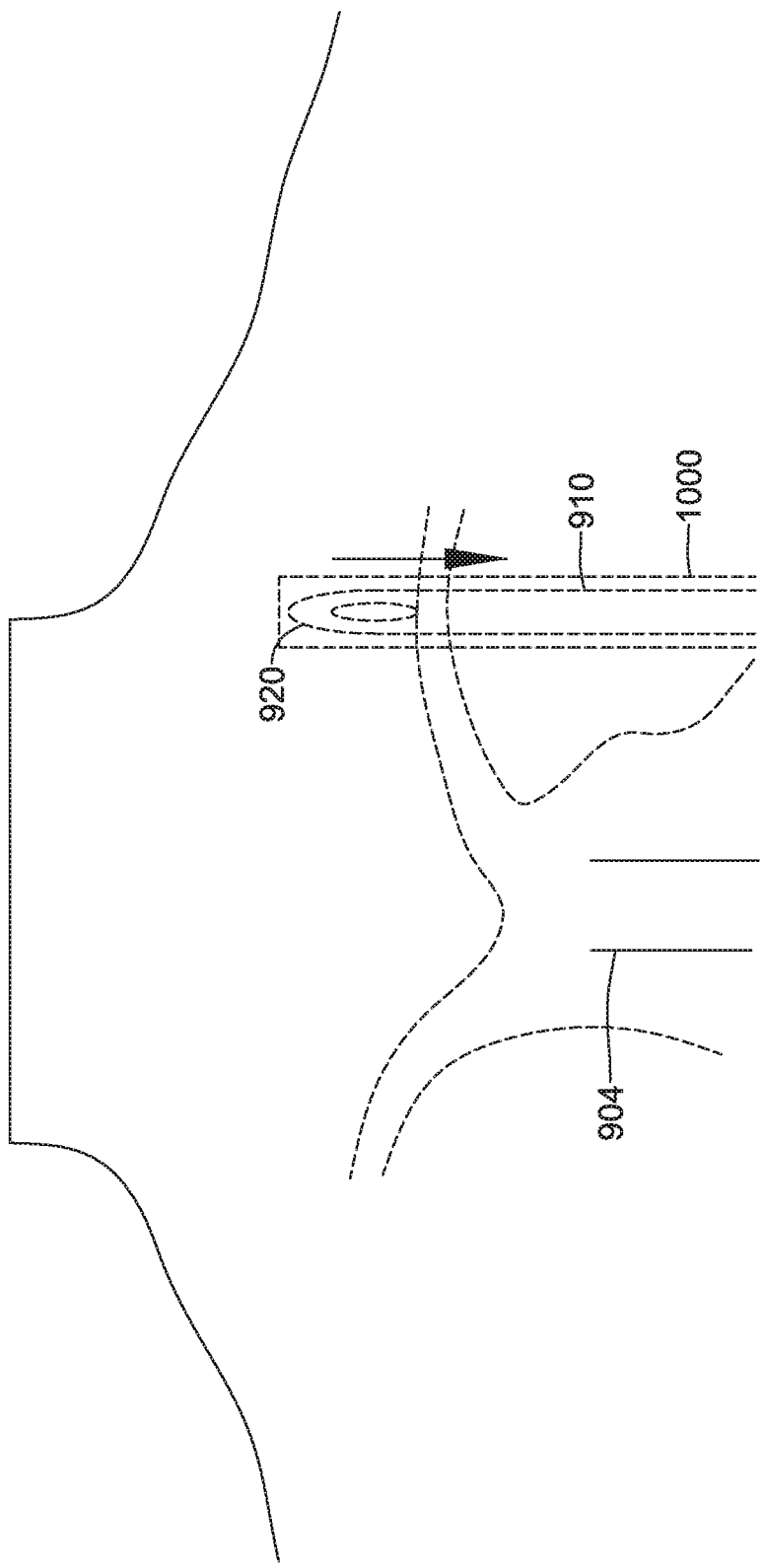

FIXATION MECHANISM FOR AN IMPLANTABLE LEAD

CROSS REFERENCE TO RELATED APPLICATIONS

The present application claims the benefit of and priority to U.S. Provisional Patent Application Ser. No. 62/547,187, titled FIXATION MECHANISM FOR AN IMPLANTABLE LEAD, filed on Aug. 18, 2017, the disclosure of which is incorporated herein by reference.

BACKGROUND

The subcutaneous implantable cardioverter-defibrillator (S-ICD System) from Boston Scientific is implanted, according to the original FDA labeling, with a subcutaneous lead extending from a subcutaneous canister located in the left axilla, over the ribs to a location near the xiphoid process and then superiorly along the left side of the sternum. A three incision implant method for placement of the lead would include an incision at the device pocket in the left axilla, another incision near the xiphoid, and a third incision superior of the xiphoid incision and to the left of the sternum. Elimination of one or more incisions is desired to reduce potential avenues for infection into the body, as well as to improve cosmetic results by reducing the number of scars. However, early experience with chronic system implants suggests that fixation of the lead is a potential concern. Thus there is great interest in innovations to simplify the implant procedure and enhance fixation of the lead. New and alternative methods and devices for securing a lead, in particular at a subcutaneous location, or other positions, whether for the S-ICD System or other devices, are desired.

OVERVIEW

The present inventors have recognized that a new and useful innovation may include a tool and method of using a tool for aiding in the placement of a fixation device on a lead. Such a tool may be used to place a fixation device on a distal portion of a lead.

A first illustrative and non-limiting example is a fixation device placement tool for use with: a lead having a lead proximal end and a lead distal end having a lead distal tip having an outer diameter; and a fixation device having a body with a lumen therethrough and at least one securing mechanism integral with or attached to the body, wherein the lumen of the fixation device is smaller than the outer diameter of the lead distal tip; the tool comprising a tool body having a tool proximal end and a tool distal end, the proximal end having a cavity for receiving the lead distal tip, the tool distal end having a tool distal tip, the tool distal tip having a first tool outer diameter which is smaller than the inner diameter of the fixation device lumen, the tool proximal end having a second tool outer diameter which is greater than the inner diameter of the fixation device lumen, the body having an outer surface with a tapered portion that expands from a third tool outer diameter that is less than the inner diameter of the fixation device lumen to the second tool outer diameter; such that the tool is configured to allow a user to place the tool proximal end over the distal tip of the lead and pass the fixation device over the tool to stretch the fixation device and facilitate placement of the fixation device on the lead.

Additionally or alternatively to the first illustrative, non-limiting example, the tool may further comprise a first intermediate portion having a third outer diameter and a second intermediate portion having a fourth outer diameter, wherein the first intermediate portion is proximal of the second intermediate portion, and the fourth outer diameter is greater than the third outer diameter but less than the second outer diameter.

Additionally or alternatively to the first illustrative, non-limiting example, the fourth outer diameter may be equal to or greater than the inner diameter of the fixation device lumen, such that the fixation device can be securely maintained on the first intermediate portion of the tool.

Additionally or alternatively to the first illustrative, non-limiting example, at least a portion of the cavity may have an inner diameter that is equal to or less than the outer diameter of the lead distal tip; and the tool proximal end may be made of a flexible material that can be stretched to allow the cavity to receive and become at least temporarily secured to the lead distal tip.

Additionally or alternatively to the first illustrative, non-limiting example, the tool may further comprise a lubricant on at least the tapered portion thereof.

A further example relating to the first illustrative non-limiting example may comprise a method of preparing a lead having a distal tip having an outer diameter for implantation in a patient using a tool as in the first illustrative, non-limiting example (and any variant thereof) and a fixation device having a body with a lumen therethrough and at least one securing mechanism integral with or attached to the body, wherein the lumen of the fixation device is smaller than the outer diameter of the lead distal tip, the method comprising: placing the proximal end of the tool over the distal tip of the lead; advancing the fixation device over the tool from the tool body distal end to the tool body proximal end, thereby stretching or expanding the fixation device lumen; placing the fixation device on the lead by passing the fixation device from the proximal end of the tool onto the lead; and removing the tool from the distal tip of the lead.

A second illustrative, non-limiting example takes the form of a combination tool and fixation device for use with an implantable medical lead, comprising a tool as in the first illustrative, non-limiting example or any variant thereof, and a fixation device having a body with a lumen therethrough and at least one securing mechanism integral with or attached to the body, wherein the lumen of the fixation device is smaller than the second outer diameter of the tool.

Additionally or alternatively to the second illustrative, non-limiting example, the fixation device may comprise a plurality of securing mechanisms thereon.

Additionally or alternatively to the second illustrative, non-limiting example, the one or more fixation device securing mechanisms may be made of a flexible polymer.

Additionally or alternatively to the second illustrative, non-limiting example, the one or more fixation device securing mechanisms may be metal hooks.

Additionally or alternatively to the second illustrative, non-limiting example, the one or more fixation device securing mechanisms may comprise a shape memory metal wire having a collapsed configuration and an expanded configuration, wherein the shape memory metal wire is formulated to transition to the expanded configuration when warmed from room temperature to body temperature.

Additionally or alternatively to the second illustrative, non-limiting example, the fixation device body may have a slot therethrough to facilitate expansion of the fixation device when it is slid over the proximal end of the tool.

Additionally or alternatively to the second illustrative, non-limiting example, the fixation device body may be solid about the entire circumference of the lumen.

Additionally or alternatively to the second illustrative, non-limiting example, the combination may be provided as a kit wherein the fixation device is placed on the tool within the kit.

A further example relating to the second illustrative non-limiting example may comprise a method of preparing a lead having a distal tip for implantation in a patient using a combination or kit as in the second illustrative, non-limiting example, comprising placing the proximal end of the tool over the distal tip of the lead; advancing the fixation device over the tool from a location of the third outer diameter over the tapered portion of the tool to the tool proximal end, thereby stretching or expanding the fixation device lumen; placing the fixation device on the lead by passing the fixation device from the proximal end of the tool onto the lead; and removing the tool from the distal tip of the lead.

A third illustrative, non-limiting example takes the form of a method of preparing a lead for implantation in a patient, the method using: a lead having a proximal end adapted for coupling to an implantable medical device, and a distal end having a distal tip; a fixation device having a body with a lumen therethrough and at least one securing mechanism integral with or attached to the body; and a tool for fixation device placement, the tool having a proximal end with a cavity adapted to receive the distal end of the lead, a distal end sized to fit within at least a portion of the lumen of the fixation device and a medial portion between the tool proximal and distal ends, wherein an outer surface of the fixation device is tapered between the medial portion and the proximal end such that the proximal end has a larger outer diameter than the medial portion; the method comprising: placing the distal tip of the lead into the cavity of the tool; and sliding the fixation device from the medial portion of the tool toward and over the proximal end of the tool and onto the lead; wherein during the sliding step the inner diameter of the fixation device lumen is expanded by the tapered outer surface of the tool.

Additionally or alternatively to the third illustrative, non-limiting example, the method may further comprise removing the tool from the distal tip of the lead.

Additionally or alternatively to the third illustrative, non-limiting example, the proximal end of the tool may be comprised of a flexible material configured to stretch over the distal tip of the lead allowing the cavity to receive the distal tip portion of the lead.

Additionally or alternatively to the third illustrative, non-limiting example, the body of the fixation device may be comprised of a flexible material configured to stretch, allowing the fixation device to move over the tool and the distal tip portion of the lead.

Additionally or alternatively to the third illustrative, non-limiting example, a portion of the lead may include a groove or depression configured to receive the fixation device and hold the fixation device in place on the lead.

Additionally or alternatively to the third illustrative, non-limiting example, the at least one securing mechanism of the fixation device may have a first end coupled to the body and a second end adapted to extend away from the body, wherein the securing mechanism may be configured for both a collapsed position for use during implantation and an extended position to impede movement relative to patient tissue, and the method may further comprise placing a sheath over a portion of the lead including the fixation device to constrain the at least one securing mechanism in the collapsed configuration for implant. This alternative may also apply to methods associated with each of the first and second illustrative non-limiting examples.

Additionally or alternatively to the third illustrative, non-limiting example, the at least one securing mechanism may include a first securing mechanism and a second securing mechanism and the first securing mechanism may have a first degree of angular separation with the body that is substantially equal to a second degree of angular separation of the second securing mechanism with the body.

Additionally or alternatively to the third illustrative, non-limiting example, the at least one securing mechanism may include a shape memory metal material therein and, when the sheath is placed on the at least one securing mechanism, the shape memory metal can be readily collapsed, while once in the body of the patient during insertion of the device, the shape memory metal exerts force to adopt the extended position.

Additionally or alternatively to the third illustrative, non-limiting example, the method may comprise advancing the lead and the fixation device through an incision and to a desired location in the patient. Additionally or alternatively, the method may further comprise, prior to advancing the lead and the fixation device to the desired location in the patient, placing a sheath over the lead after the fixation device is placed on the lead, such that the sheath constrains the at least one securing mechanism of the fixation device; and after advancing the lead and the fixation device to the desired location in the patient, removing the sheath to release the at least one securing mechanism of the fixation device.

A fourth illustrative, non-limiting example is a fixation device placement tool for use with a lead having a lead proximal end and a lead distal end having a lead distal tip having an outer diameter; and a fixation device having a body with a lumen therethrough and at least one securing mechanism integral with or attached to the body, wherein the lumen of the fixation device has an inner diameter that is smaller than the outer diameter of the lead distal tip; the tool comprising a tool body having a tool proximal end and a tool distal end, the tool proximal end having a cavity for receiving the lead distal tip, the tool distal end having a first tool outer diameter which is smaller than the inner diameter of the fixation device lumen, the tool proximal end having a second tool outer diameter which is greater than the inner diameter of the fixation device lumen, the body having an outer surface with a tapered portion that expands from a third tool outer diameter that is less than the inner diameter of the fixation device lumen to the second tool outer diameter; wherein the tool is configured to allow a user to place the tool proximal end over the distal tip of the lead and pass the fixation device over the tool to stretch the fixation device and facilitate placement of the fixation device on the lead.

Additionally or alternatively to the fourth illustrative, non-limiting example, the tool may further comprise a first intermediate portion having the third outer diameter and a second intermediate portion having a fourth outer diameter, wherein the first intermediate portion is proximal of the second intermediate portion, and the fourth outer diameter is greater than the third outer diameter but less than the second outer diameter. Additionally or alternatively the fourth outer diameter may be equal to or greater than the inner diameter of the fixation device lumen, such that the fixation device can be securely maintained on the first intermediate portion of the tool.

Additionally or alternatively to the fourth illustrative, non-limiting example, at least a portion of the cavity may have an inner diameter that is equal to or less than the outer diameter of the lead distal tip; and the tool proximal end is made of a flexible material that can be stretched to allow the cavity to receive and become at least temporarily secured to the lead distal tip.

Additionally or alternatively to the fourth illustrative, non-limiting example, the tool may further comprise a lubricant on at least the tapered portion thereof.

A fifth illustrative, non-limiting example takes the form of a combination tool and fixation device for use with an implantable medical lead having a lead distal tip, the combination comprising a fixation device having a body with a lumen therethrough having an inner diameter and at least one securing mechanism integral with or attached to the body; a tool body having a tool proximal end and a tool distal end, the tool proximal end having a cavity for receiving the lead distal tip, the tool distal end having a first tool outer diameter which is smaller than the inner diameter of the fixation device lumen, the tool proximal end having a second tool outer diameter which is greater than the inner diameter of the fixation device lumen, the body having an outer surface with a tapered portion that expands from a third tool outer diameter that is less than the inner diameter of the fixation device lumen to the second tool outer diameter; wherein the tool is configured to allow a user to place the tool proximal end over the distal tip of the lead and pass the fixation device over the tool to stretch the fixation device and facilitate placement of the fixation device on the lead.

Additionally or alternatively to the fifth illustrative, non-limiting example, the one or more fixation device securing mechanisms may be made of a flexible polymer.

Additionally or alternatively to the fifth illustrative, non-limiting example, the one or more fixation device securing mechanisms may be metal hooks.

Additionally or alternatively to the fifth illustrative, non-limiting example, the fixation device body may have a slot therethrough to facilitate expansion of the fixation device when it is slid over the proximal end of the tool.

Additionally or alternatively to the fifth illustrative, non-limiting example, the fixation device body may be solid about the entire circumference of the lumen.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 9A-9F show a three incision method for implanting a lead;
FIGS. 10A-10E show a two incision method for implanting a lead.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives. In the methods shown below, structures may be beneath the skin and over the ribcage of the patient, though such elements are not always shown in phantom.

The words "proximal" and "distal" are used herein to differentiate the ends of devices. No specific anatomical significance is intended. For example, the distal end of a lead is not necessarily anatomically distal relative to the proximal end of the lead; anatomic distal and proximal terminology will be determined by the final implantation location(s).

Figure 1A:
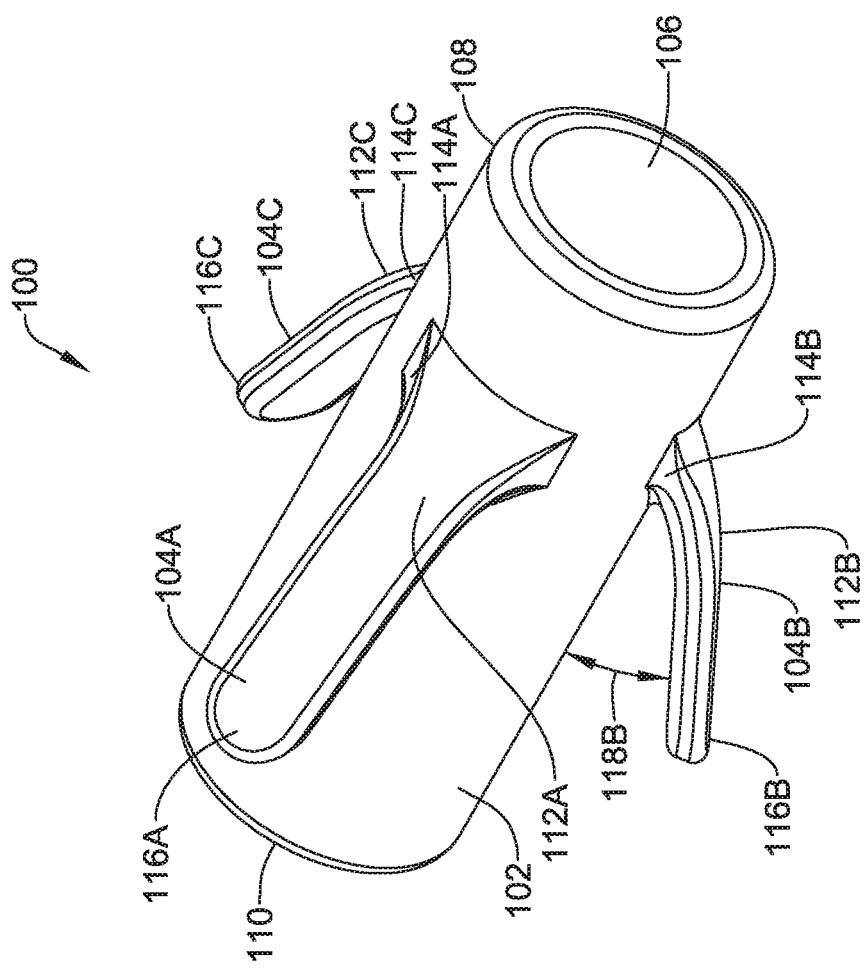
FIG. 1A shows a first exemplary fixation device.

FIG. 1A shows an exemplary fixation device 100. As shown, the fixation device may include a body 102 and securing mechanisms 104A-104C. According to various embodiments, the body 102 may define a lumen 106 that extends from an open distal end 108 to an open proximal end 110.

The body 102 may be formed of any biocompatible material suitable for chronic implantation in a patient. Some examples include soft thermoplastic materials, polyurethanes, silicone rubbers, nylon, polyethylenes, fluorinated hydrocarbon polymers, and the like. In some embodiments, the body 102 may include a highly flexible material such as low density polyethylene (LDPE), polyvinylchloride, THV, etc. In some instances, the body 102 may be formed from or comprise, for example, stainless steel, such as high tensile stainless steel, or other materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, nickel-titanium alloys (e.g., nitinol), etc. The body 102 may be formed from a lubricious polymer, such as a fluorocarbon (e.g., polytetrafluoroethylene (PTFE)), a polyamide (e.g., nylon), a polyolefin, a polyimide, or the like). Additional polymeric materials which may make up the body 102 include polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. For example, the body 102 may be formed by extruding a rigid thermoplastic elastomer polymer.

The body 102 may be colored to enhance surgical visibility by, for example, incorporating some amount of titanium dioxide. The body may also be doped with or include a component made with a radiopaque material such as barium sulfate ($BaSO_4$), bismuth trioxide ($Bi_2O_3$), bismuth subcarbonate ($Bi_2O_2CO_3$), bismuth oxychloride (BiOCl), and tungsten. Still in further embodiments, the body 102 may be composed of a combination of several these materials either as a mixture or as a series of layers or parts that are combined, molded, welded or otherwise joined together.

In an example, the inner diameter of the lumen 106 may be equal to or slightly less than an outer diameter of a portion of an implantable lead that the device 100 is designed to function with. The lumen 106 may have a single diameter or, in other examples, the lumen 106 may have a diameter that varies along the length of the body 102. In some examples, the diameter of the lumen 106 may be largest at the open proximal end 110, may taper along the length of the body 102, and may be smallest at the open distal end 108. This may be beneficial for allowing the fixation device 100 to more easily fit around and be placed onto an application tool, described further below, and moved onto a lead, also described further below. In some examples the body 102 may be stretchable or elastic to allow the size of the lumen 106 to expand to allow passage over a distal portion of an implantable lead.

According to various embodiments, the securing mechanisms 104A-104C may be located near the distal end 108 of the body 102 and may be configured to push against and engage tissue of a patient when the fixation device is implanted inside the patient. In some cases, the securing mechanisms 104A-104C may be flaps that are a formed, single-piece, with the body 102 by molding and/or cutting processes. In some cases, the securing mechanisms 104A-104C may have first ends 112A-112C attached to the body 102 in any suitable manner, which may include mechanical structure such as hinges, screws, pins and/or any other suitable fastener, or bonding such as through the use of a medical adhesive. Heat shrink tubing may be placed over the first ends 112A-112C for securing to the body 102, or laser, sonic, heat, or other welding process may be used to attach the first ends 112A-112C to the body 102.

In some cases, the first ends 112A-112C may be molded to the distal end 108 so that joints 114A-114C are formed at the distal end 108. In some cases, the joints 114A-114C may be configured to pivot so that second ends 116A-116C of the securing mechanisms 104A-104C move, retract, or compress towards the body 102 to a compressed state in a hinged fashion. Alternatively, the securing mechanisms 104A-104C may be flexible to allow a compressed state to be adopted by applying force thereto. In some cases, the joints 114A-114C may be further configured to pivot so that the second ends 116A-116C move, swing, or extend away from the body 102 to an extended state.

The securing mechanisms 104A-104C may be made of any biocompatible material to allow for chronic implantation in a patient. For example, any of the materials discussed above relative to the body 102 may be used. In some examples, the securing mechanisms 104A-104C may be made of the same material as the body 102. In other examples, the securing mechanisms 104A-104C may be comprised of different materials than the body 102. In certain embodiments, the securing mechanisms 104A-104C may be comprised of a different, stiffer, material than the body 102. According to various embodiments, multiple durometers may be used with the securing mechanisms 104A-104C, for example, using a Shore hardness in the range of about 30 A to 80 A. For example, a securing mechanism 104A-104C may be formed of a harder or stiffer material closer to the body 102, and a softer or more flexible material farther from the body 102. In another example, a securing mechanism 104A-104C may be formed over a wire which may extend to or terminate short of the second end 116A-116C thereof.

According to various embodiments, the securing mechanisms 104A-104C may be configured to be collapsed by a sheath to a pre-deployed state. The fixation device may be placed on a lead and then inserted into a patient with a sheath thereover holding the securing mechanisms in the pre- deployed state. Once the fixation device 100 is in a desired position during implantation in the patient, the sheath may be removed. Upon removal of the sheath, the securing mechanisms 104A-104C may expand to engage, push against, and/or anchor the fixation device 100 to patient tissue, thereby anchoring a lead.

In various embodiments, the securing mechanisms 104A-104C may be tine shaped, hook shaped, fan shaped, a combination thereof, etc. The securing mechanisms 104A-104C may have second ends 116A-116C of any suitable shape, including without limitation, rounded, square, pointed, convex, barbed, etc.

As depicted in FIG. 1A, there may be several securing mechanisms 104A-104C are radially spaced from one another around the body 102. For example, the securing mechanisms may be symmetrically located around the body 102. In some cases, the securing mechanisms 104A-104C may be limited to one side of the body 102. In some instances, there may be a single securing mechanism. In some examples, the securing mechanisms 104A-104C may each be similar in design/structure, or, in other examples, the width, length, shape, or other features of the securing mechanisms 104A-104C may vary from one another.

In some examples, the securing mechanisms 104A-104C may be attached to or configured relative to the body 102 such that the securing mechanisms 104A-104C have a desired degree of angular separation, as indicated at 118B, with the body 102. For example, in some cases, the joints 114A-114C may be configured so that there is a 45° angle of separation 118B between the securing mechanisms 104A-104C and the body 102 in a relaxed, non-compressed state. In some cases, the angle of separation 118B may be 15°, 30°, 60°, 90°, etc. In some cases, the angles of separation 118B may be equal such that the securing mechanisms 104A-104C are orientated in a symmetric configuration. In some cases, the angles of separation 118B may not be the same or equal to one another such that the securing mechanisms 104A-104C are orientated in an asymmetric configuration.

Figure 1B:
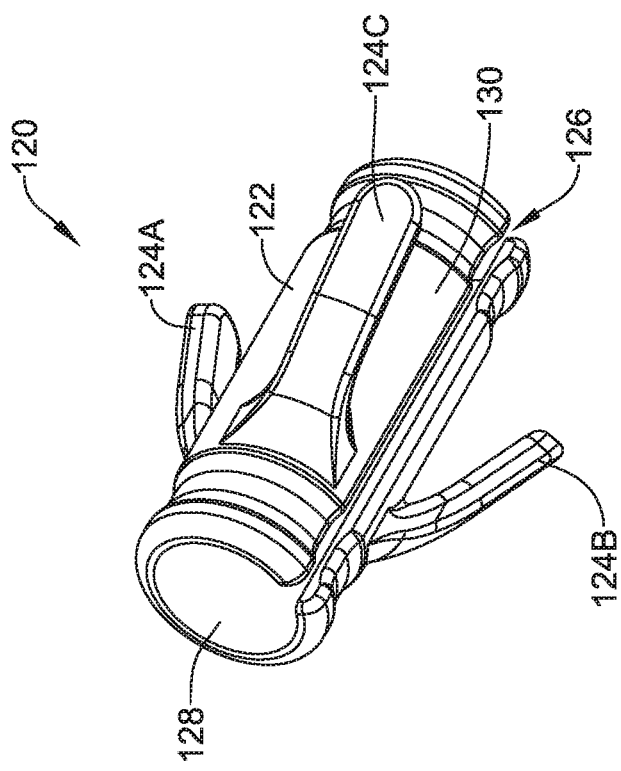
FIG. 1B shows a second exemplary fixation device.

FIG. 1B shows a second exemplary fixation device 120. As shown, the fixation device may include a body 122 and securing mechanisms 124A-124C. The configuration and operation of the fixation device 120 may be similar to that of the fixation device 100 described in regard to FIG. 1A. However, as can be seen in this embodiment, the body 122 includes a gap 126 that extends from an outer surface 130 of the body 122 to a lumen 128 and may enable the body 122 to move onto a lead and couple the fixation device 120 to the lead. For example, the fixation device 120 may be pressed against the lead and the lead may move through the gap 126 and into the lumen 128. As such, the body 122 may substantially surround the lead and hold the fixation device 120 onto the lead. If desired, a groove may extend circumferentially around the fixation device 120 to aid in the placement of a suture thereabout, in order to allow a physician to secure the device 120 at a desired position on the lead.

Figure 2:
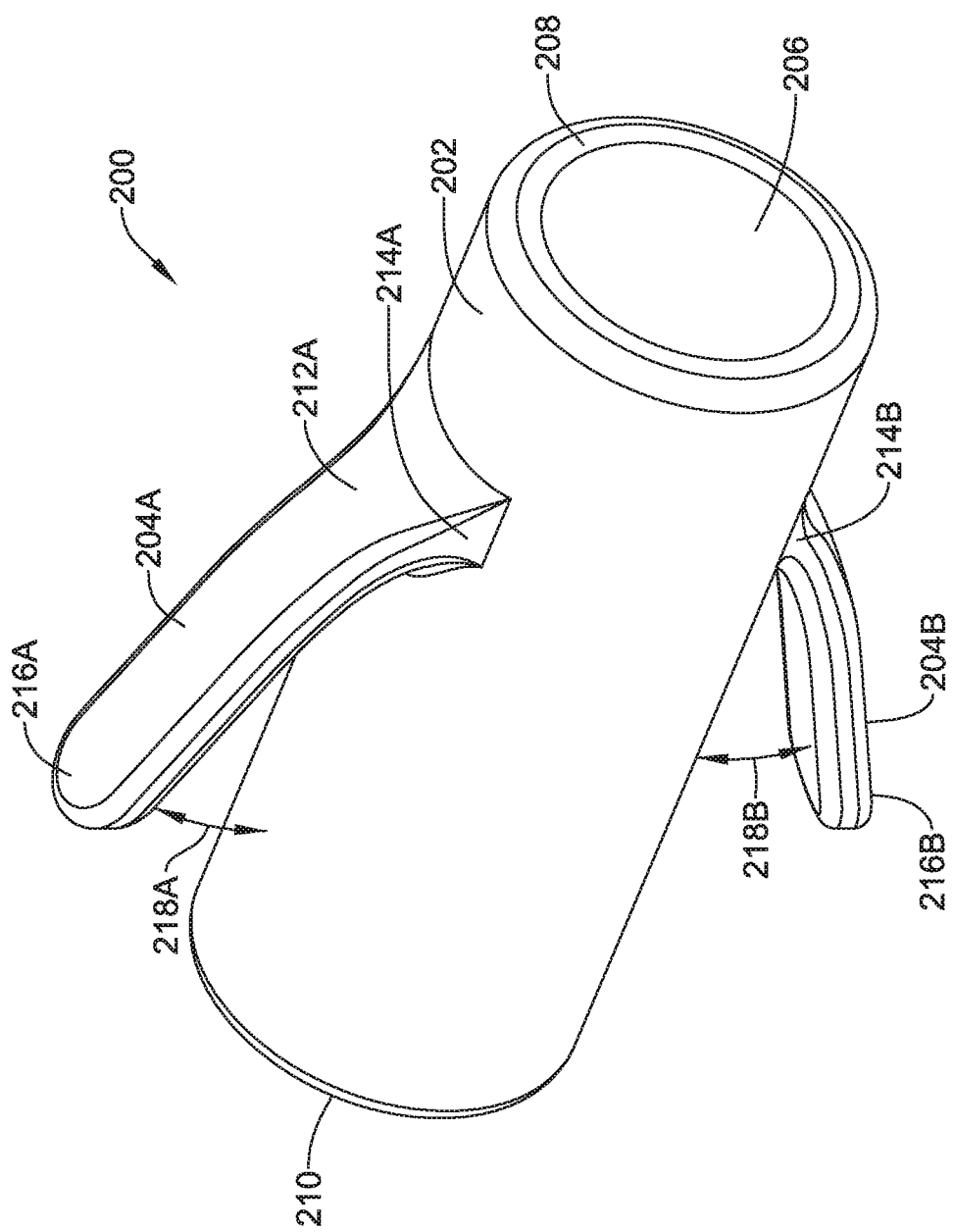
FIG. 2 shows a third exemplary fixation device.

FIG. 2 shows a third exemplary fixation device 200. As shown, the fixation device 200 may include a body 202 and securing mechanisms 204A-204B, with a bore or lumen 206 extending therethrough between a distal end 208 and a proximal end 210. As may be seen in FIG. 2, a multilayer body 202 may be used with an inner layer and an outer layer (additional layers may be provided, if desired); for example, a lubricious material (PTFE for example) may be used for the inner layer, with a softer and bondable layer for attaching to the securing mechanisms 204A-204B as an outer layer. The configuration and operation of the fixation device 200 may be similar to that of the fixation device 100 described in regard to FIG. 1A. Thus the device 200 is shown having securing mechanisms 204A-204B with first ends 212A-212B attached to the body 202 at joints 214A-214B, extending therefrom to second ends 216A-216B and defining angles (in a relaxed state) as noted at 218A-218B. However, as can be seen in this embodiment, the fixation device 200 has only two securing mechanisms 204A-204B configured to push against tissue of a patient.

Figure 3:
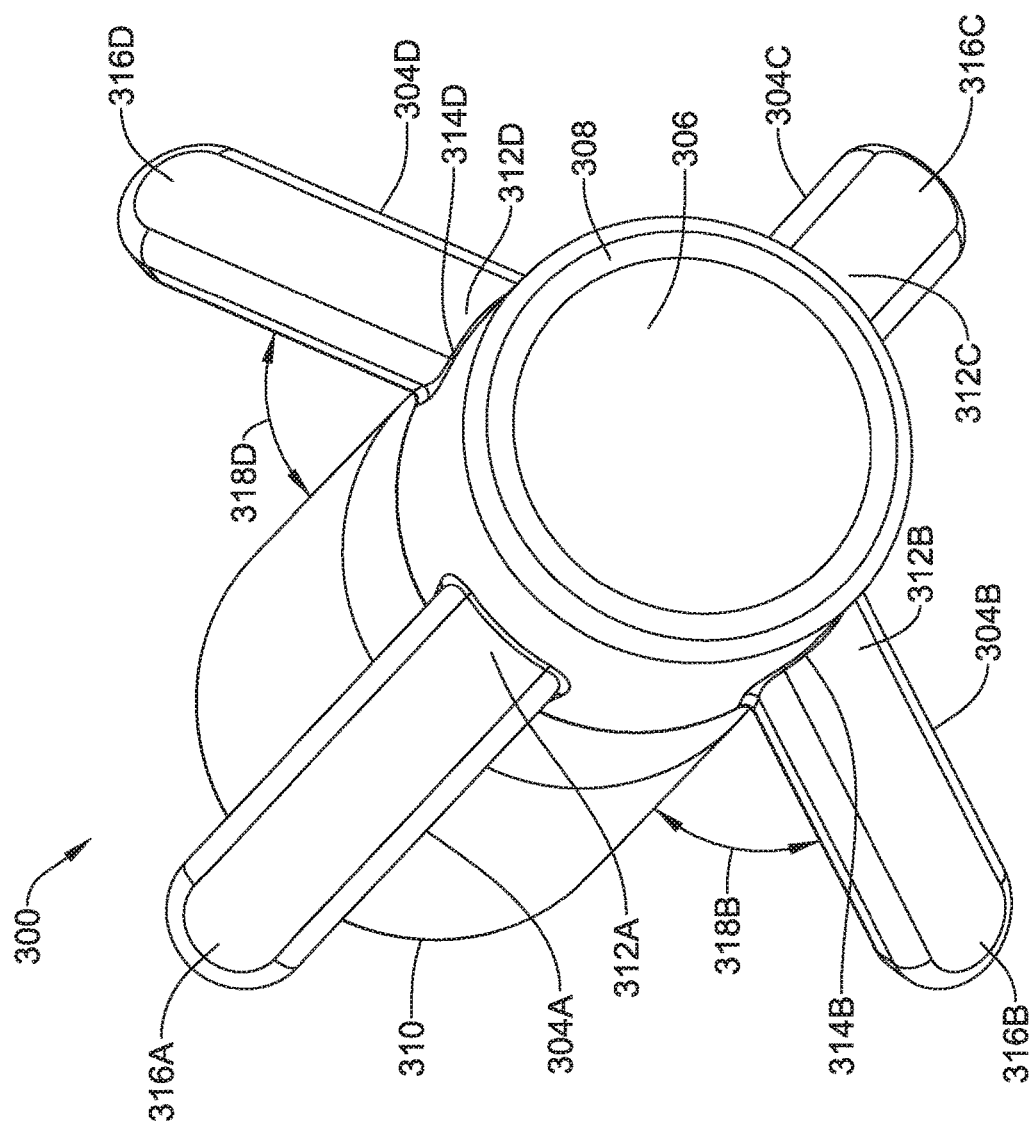
FIG. 3 shows a fourth exemplary fixation device.

FIG. 3 shows a fourth exemplary fixation device 300. As shown, the fixation device 300 may include a body 302 and securing mechanisms 304A-304D. The configuration and operation of the fixation device 300 may be similar to that of the fixation device 100 described in regard to FIG. 1. However, as can be seen in this embodiment, the fixation device 300 has four securing mechanisms 304A-304D configured to push against tissue of a patient. Once again, the securing mechanisms 304A-304D may include first ends 312A-312D attached to the body 302, defining joints such as that at 314D, extending to second ends 316A-316D and defining angles such as those at 318B, 318D relative to the body 302 in a relaxed state. A lumen or bore 306 again extends through the device between distal end 308 and proximal end 310. A single layer or multilayer structure may be used as desired.

Figure 4A:
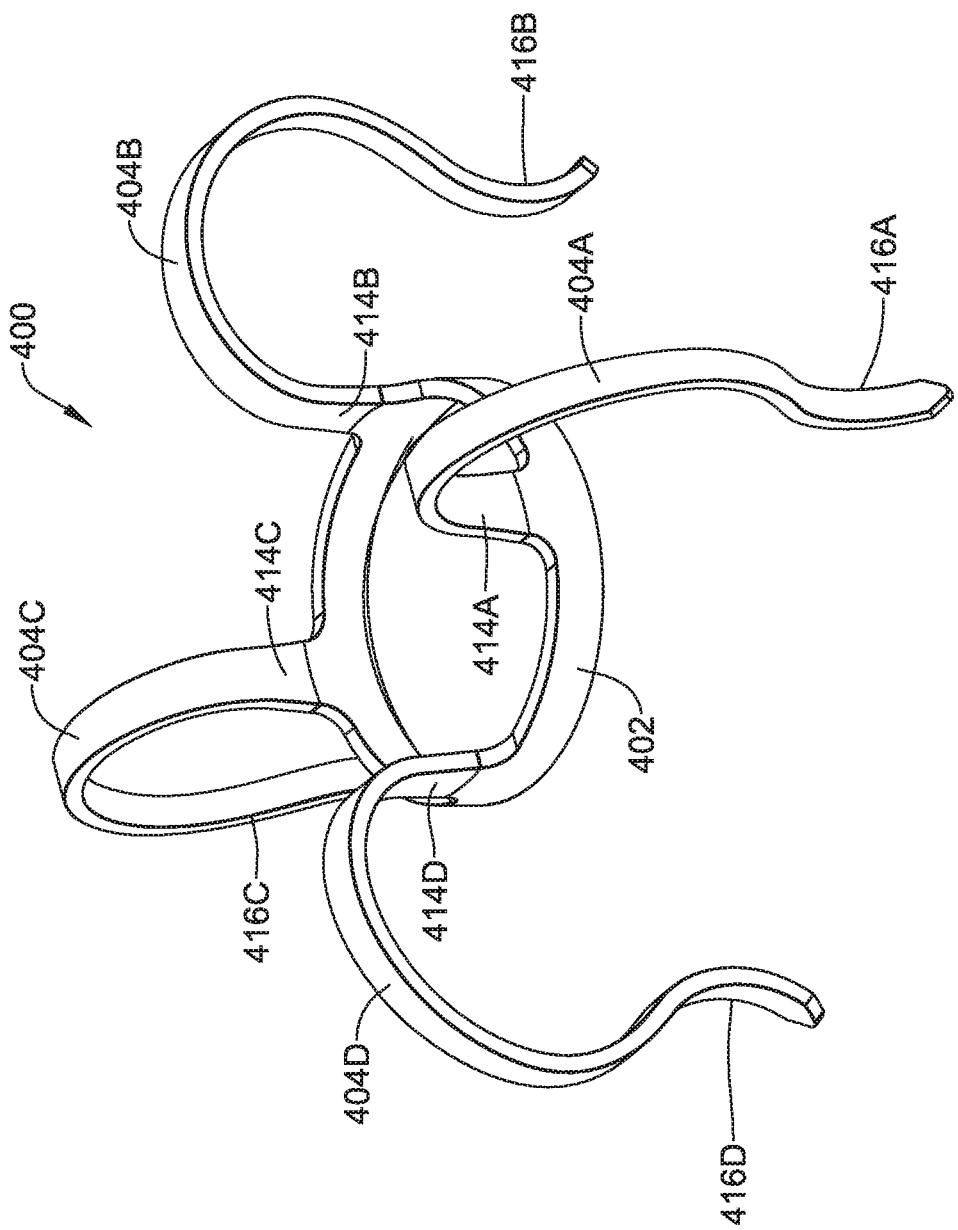
FIG. 4A shows a fifth exemplary fixation device.

FIG. 4A shows a fifth exemplary fixation device 400. As shown, the fixation device 400 may include a body 402 and securing mechanisms 404A-404D. In this embodiment, the body 402 is ring shaped and the securing mechanisms 404A-404D may be hook shaped, extending from first attached ends 414A-414D to second ends 416A-416D. Although configured differently than fixation devices 100, 120, 200, and 300, the fixation device 400 may operate similarly to the fixation devices 100, 120, 200, and 300.

In the example of FIG. 4A, the securing mechanisms may be made of a metal such as a superelastic alloy or a shape memory metal, for example, Nitinol, to allow for a collapsed state prior to implantation, using, for example a sheath to hold the securing mechanisms 404A-404D in a desired, collapsed state. For example, it is widely known in the medial arts to use Nitinol formulations that transition from a flexible and easily manipulated state to adopt a "remembered" shape upon being warmed from room temperature to body temperature. Below a reference temperature the Nitinol is superelastic, and above the reference temperature, it transitions to being a shape memory material. For example, the transition or reference temperature may be in the range of about 30 degrees Celsius to about 35 degrees Celsius, though the present invention is not intended to be limited to a specific nitinol formulation.

Prior to implantation the securing mechanisms 404A-404D can be manipulated to a collapsed state and a sheath passed over. When introduced into a patient, the change in temperature may cause the securing mechanisms to exert force on the sheath to preferentially adopt their "remembered" shape, and on removal of the sheath the securing mechanisms 404A-404D will engage surrounding tissue in order to become secured thereto. Such metal securing mechanisms may be bare, may be coated with a polymer, and/or may be coated with a substance (such as a steroid) or have a surface treatment (such as a roughened surface) to promote tissue growth and/or attachment.

Figure 4B:
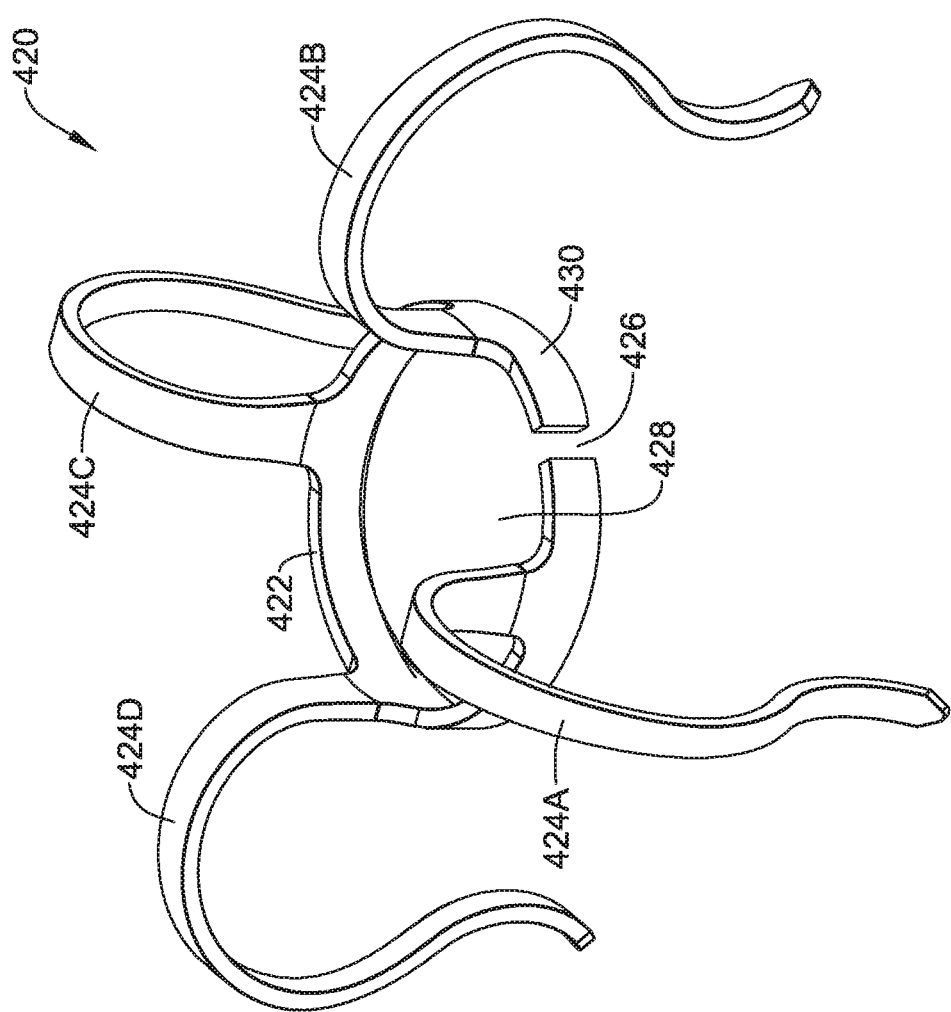
FIG. 4B shows a sixth exemplary fixation device.

FIG. 4B shows a sixth exemplary fixation device 420. As shown, the fixation device may include a body 422 and securing mechanisms 424A-424D. Similar to fixation device 400, the body 422 of the fixation device 420 may be substantially ring shaped and the securing mechanisms 404A-404D may be hook shaped. Furthermore, as can be seen in this embodiment, the body 422 includes a gap 426 that extends from an outer surface 430 of the body 422 to a lumen 428 defined by the body 422 that may enable the body 422 to move onto a lead and couple the fixation device 420 to the lead. For example, the fixation device 420 may be pressed against the lead and the lead may move through the gap 426 and into the lumen 428. As such, the body 422 may substantially surround the lead and hold the fixation device 420 onto the lead. The fixation device 420 may operate similarly to the fixation devices 100, 120, 200, and 300. In another example, the gap 426 may be used as an expansion slot to allow the inner diameter of the lumen 428 to allow the fixation device 420 to slide over a tool as shown below for sliding the fixation device onto a lead. In another example, the body 422 may have a more cylindrical design, and the exterior of the body 422 may include a circumferential groove for receiving or retaining a suture that can be tied thereon to secure the body 422 and fixation device 420 onto a lead.

Figure 5:
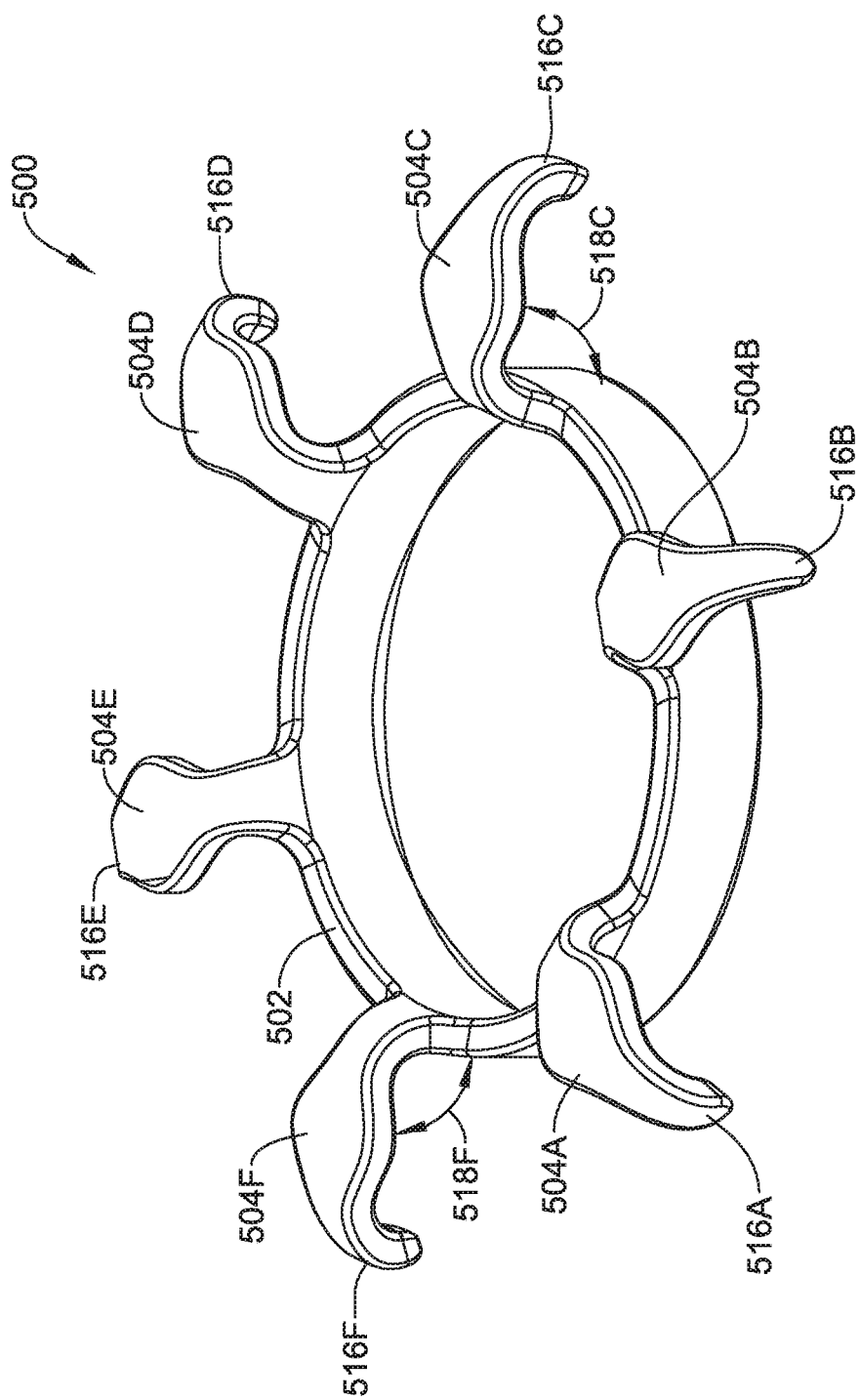
FIGS. 5-6 show a seventh exemplary fixation device.

FIG. 5 shows a seventh exemplary fixation device 500. As shown, the fixation device 500 may include a body 502 and securing mechanisms 504A-504F. Furthermore, as can be seen in this embodiment, the body 502 may be substantially ring shaped and the securing mechanisms 504A-504F may be hooked tines extending from the body at an angle illustrated by 518C, 518F, with tips 516A-516F for engaging tissue. In this embodiment, the securing mechanisms 504A-504F may be hooked to potentially prevent the securing mechanisms 504A-504F from scraping or tearing the tissue of a patient. Although configured differently than fixation devices 100, 120, 200, 300, 400, and 420, the fixation device 500 may operate similarly to the fixation devices 100, 120, 200, 300, 400, and 420. The above discussion relative to FIG. 4A of the potential use of Nitinol, coatings, and surface treatment on the securing mechanisms 504A-504F applies here as well.

Figure 6:
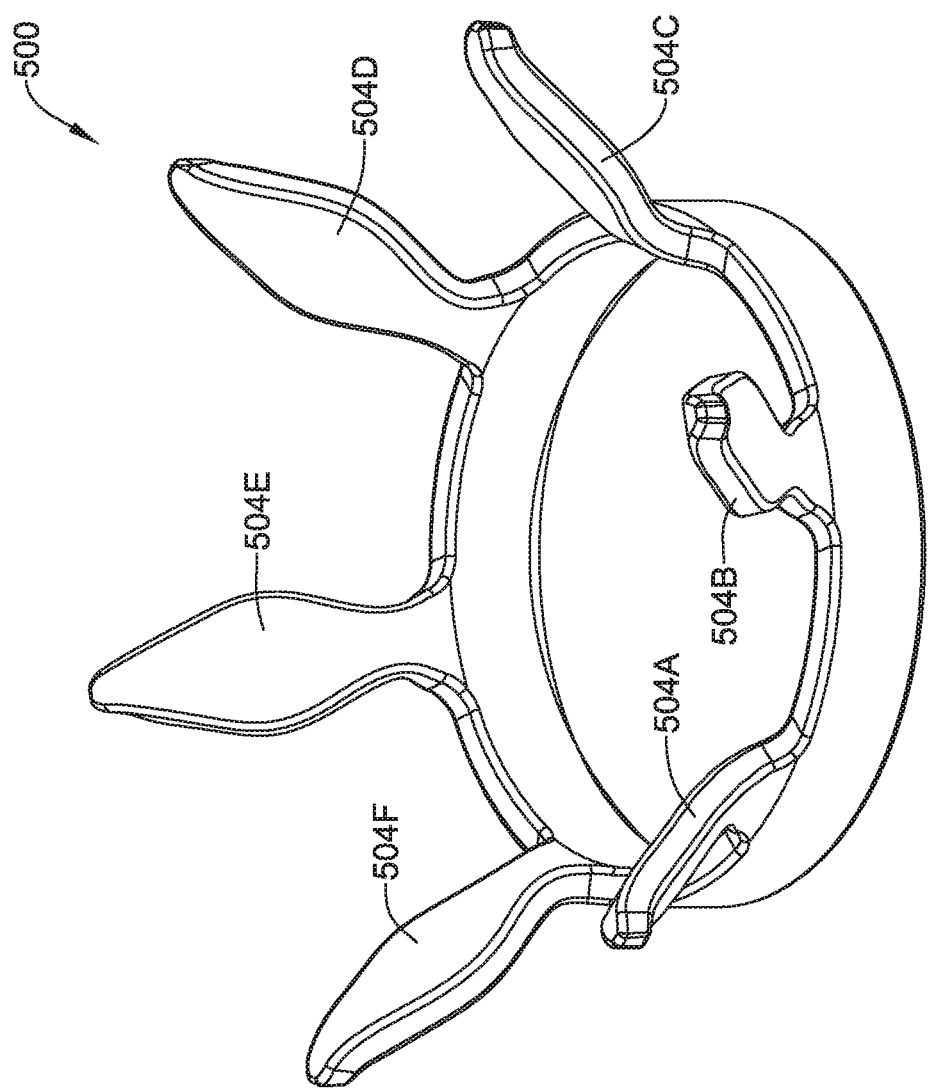

FIG. 6 shows an additional view of the device 500 of FIG. 5, with the securing mechanisms 504A-504F shown in a more compressed position, suitable for placement inside of an introducer sheath. The individual securing mechanisms may be under tension in the configuration shown, such that as an introducer sheath is removed, the mechanisms 504A-504F spring back to the configuration of FIG. 5, engaging tissue to anchor the associated lead.

The described fixation devices of FIGS. 1A-1B, 2, 3, 4A-4B and 5-6 are by no means exhaustive. In some cases, the fixation devices may include other configurations with more or fewer securing mechanisms and/or using a plurality of different types of fixation mechanisms on a single fixation device. Moreover, the examples depicted above illustrate how the fixation device may be customized to potentially optimize its performance and/or meet the requirements of the physician and patient.

For example, in certain embodiments, the fixation devices may be manufactured using 3D printing technology. This may allow customization in the clinic or hospital, where the user may manipulate the materials, quantity and shape/size of the securing mechanisms and/or body of the devices shown above. In one example, the fixation device may include six 60 A durometer, silicone, tine shaped securing mechanisms. In another example, the fixation device may include three soft 3D printed tine shaped securing mechanisms. The final design may be configured based on a multiple of factors including, but not limited to, reliability, patient comfort, implantation locations and circumstances, etc.

Figure 7:
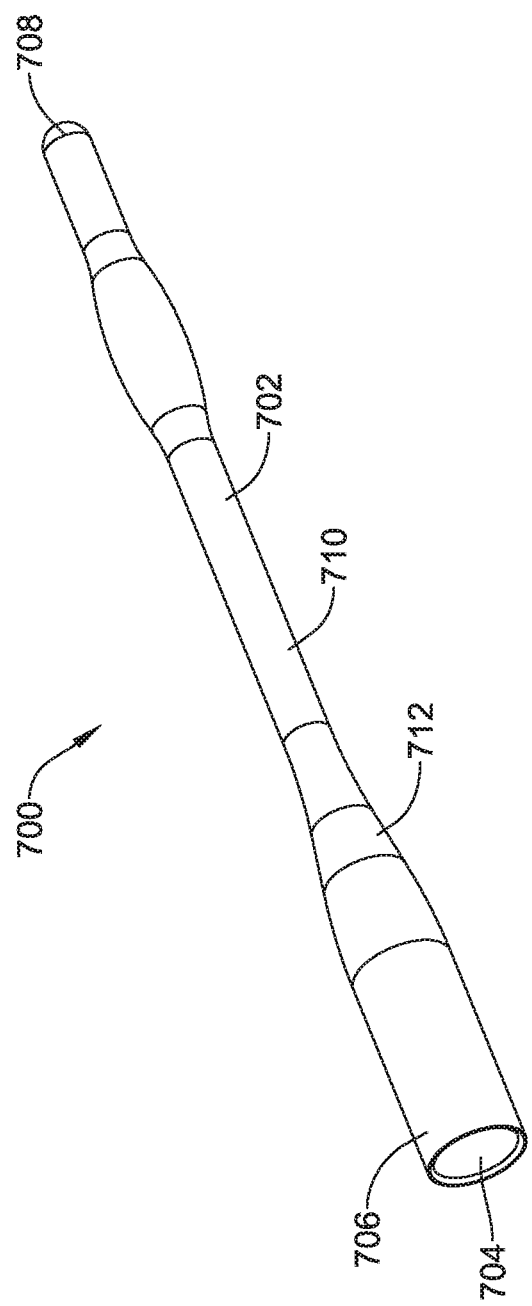
FIG. 7 shows an illustrative tool for use in some examples.

FIG. 7 shows an exemplary tool 700 adapted to transfer a fixation device (e.g., fixation device 100, 120, 200, 300, 400, 420, or 500, above) onto a lead. The tool 700 may take the form of an elongate device having an outer surface 702 that defines a cavity 704 therein. In some cases, the cavity 704 may span a portion of the length of the tool 700. In certain embodiments, the cavity 704 may span the entire length of the tool 700.

As shown in FIG. 7, the tool 700 has an open proximal end 706 and a closed distal end 708. In some cases, the distal end 708 may also be open. As shown below in FIGS. 8A-8C, the intent is that the cavity 704 at the open proximal end 706 is sized to receive the distal tip of a lead therein. The outer surface of the tool includes a tapered portion at 712 between a narrower portion at 710 and the proximal end 706. In use, a fixation device as shown above may be placed on the tool. For example, the fixation device may be preloaded by a manufacturer, or a user may place the fixation device by passing the fixation device over the distal end 708 of the tool 700.

The fixation device can be held in a relaxed state over the narrower portion 710 of the tool 700. The distal tip of the lead is inserted in the cavity 704, and the fixation device is then passed over the tapered portion 712 and proximal end 706 of the tool onto the lead. As the fixation device passes over the tapered portion 712 and proximal end 706 of the tool 700, the fixation device will be stretched to a larger inner diameter than its resting state; once past the proximal end 706 and on the lead, the fixation device preferably reduces in diameter onto the lead.

If the resting inner diameter of the fixation device is less than the outer diameter of the lead, this will lock the fixation device in place on the lead. The size of the fixation device may be in the range of 3 cm or less in length with an inner diameter in the range of about 4 to about 20 French. At these dimensions, manual handling without the tool 700 mayd be quite difficult, making the tool 700 a highly useful part of the overall system In various embodiments, the tool 700 may vary in diameter where it has a largest diameter at one portion and a smallest diameter at another portion. As such, other portions of the tool 700 may have a diameter value that lies somewhere between the largest and smallest diameter. In the example shown, the largest diameter may be located at the proximal end 706 and the smallest diameter may be located at the distal end 708. Having a diameter that is smallest at the distal end 708 may be beneficial for allowing the fixation device to more easily fit around and be placed onto the tool 700. In some cases, the tool 700 may have a smaller diameter medial portion 710 and a tapered portion 712 that allows the fixation device to gradually move onto the larger diameter proximal end 706.

In some cases, the tool 700 or at least an outer layer of the tool 700 may be formed from a lubricious polymer, such as a fluorocarbon (e.g., polytetrafluoroethylene (PTFE)), a polyamide (e.g., nylon), a polyolefin, a polyimide, for example. In some embodiments, a portion of the tool 700 may also be made of a flexible material such as low density polyethylene (LDPE), polyvinylchloride, THV, etc., to allow the proximal end 706 to stretch over a tip portion of the lead, enabling the cavity 704 to receive the tip portion, and permit the fixation device to move over the proximal end 706 and onto the lead. Still in further embodiments, the tool 700 may be composed of a combination of several of these materials.

Figure 8A:
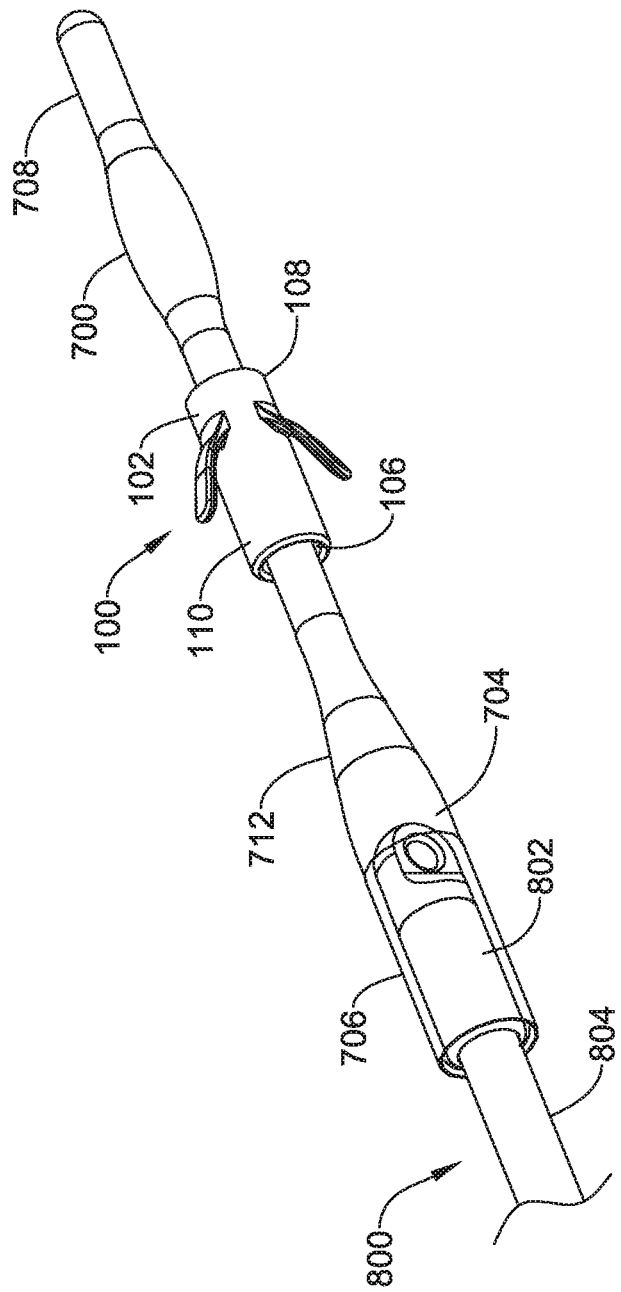
FIGS. 8A-8C show an illustrative method of preparing a lead for implantation.
Figure 8B:
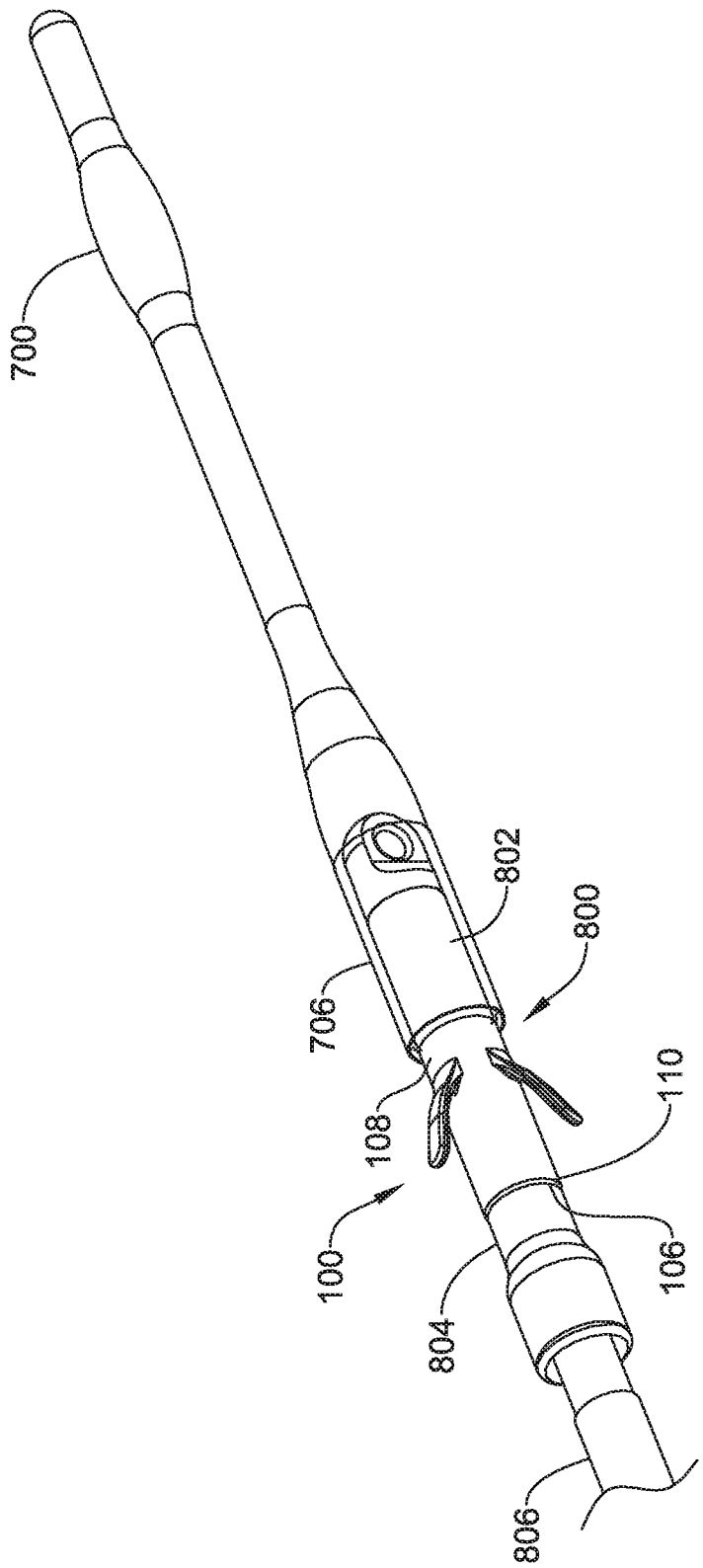
Figure 8C:
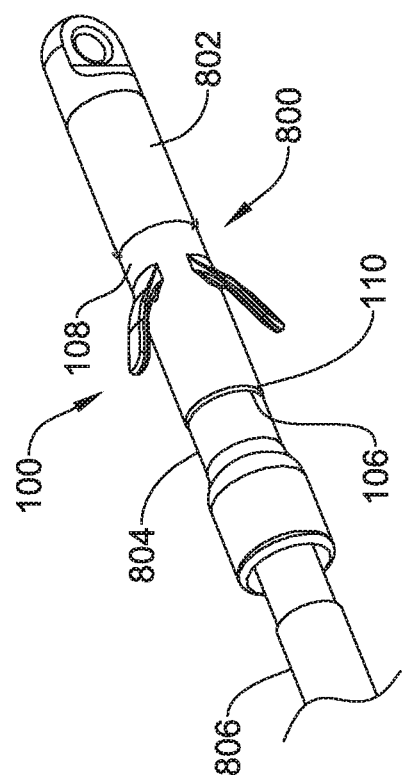

FIGS. 8A-8C illustrate an example of preparing a lead for implantation in a patient. According to various embodiments, the outer diameter of the proximal end 706 of the tool 700 and an outer diameter of a distal tip portion 802 of the lead 800 may be similar to one another and may also be in the range of between 1 French and 20 French. As discussed above and as shown in FIG. 8A, the proximal end 706 may be formed of a suitable flexible material so that it may be stretched over the distal tip portion 802. Alternatively, the cavity at the proximal end 706 of the tool may be sized to match or be slightly larger than the distal tip portion 802 of the lead 800. Accordingly, the cavity 704 may receive the distal tip portion 802 and as a result, the tool 700 may be coupled to the lead 800. The cavity may be tapered to have a larger diameter at its proximal end, and then narrowing along its length such that a lead tip may be easily inserted in the wider diameter portion and advanced to a narrower region to become secured to the tool 700.

The tool 700 may have a varying outer diameter along its length. In certain embodiments, the outer diameter near the distal end 708 of the tool 700 may be smaller than an inner diameter of the fixation device 100. This may allow the fixation device 100 to fit around and be placed onto the tool 700 as shown in FIG. 8A. In some cases, a lubricating substance, such as silicone oil may be applied to the inner diameter of the fixation device 100 during manufacturing or use to facilitate ease of placement and movement of the fixation device 100 on the tool 700. The fixation device 100 may then be moved along the tool 700 till it reaches the tapered portion 712. In certain embodiments, the tapered portion 712 may have an outer diameter that is initially smaller than the inner diameter at the proximal end 110 of the fixation device 100. However, as the fixation device 100 moves along the tapered portion 712, the outer diameter of the tool becomes large enough to force the device to stretch. Accordingly, as the fixation device 100 moves along the tapered portion 712, the body 102 may be stretched to accommodate the increased outer diameter of the tool. The body 102 may continue to be stretched till its inner diameter is large enough to accommodate the greatest outer diameter at the proximal end 706 of the tool 700. In some examples, the body 102 may include a slot (such as in FIGS. 1B and 4B) to accommodate such stretching.

Turning to FIG. 8B, the fixation device 100 has been moved over the proximal end 706 of the tool, over the distal tip portion 802 of the lead, and onto a desired location on the lead 800. In certain embodiments, the lead 800 may include a groove, indention, or depression 804 to receive the fixation device 100. In this embodiment, the groove 804 may hold or impede the fixation device 100 from moving proximally along the lead 800 and onto the electrode 806 and hold or impede the fixation device 100 from moving distally along the lead to the distal tip portion 802 and potentially off the lead 800.

In other examples, a groove, indentation or depression 804 on the lead may be omitted. For example, the inner diameter of the lumen of the fixation device 100 may match or be smaller than the outer diameter of the target location on the lead 800, such that the fixation device 100 exerts pressure on the lead 800 to secure it thereon. The fixation device 100 may alternatively have a groove or notch thereon for receiving a suture that can be used to tie the fixation device 100 onto the device, though in several examples herein, no such suture groove or notch is provided and the fixation device 100 is instead intended to become fixed in place on the lead without the use of a suture.

Turning to FIG. 8C, once the fixation device 100 has been moved into a desired position on the lead 800, the tool 700 may be removed from the distal tip portion 802.

The tool 700 may be removed in any suitable manner, such as cutting the proximal end 706, rolling the proximal end 706 off the distal tip portion 802, pulling the tool 700 in the opposite direction of the lead 800, etc. Once the tool 700 has been removed, the lead 800 may now be ready for implantation into the patient or ready for further preparation as necessary, such as placement of a sheath to constrain the securing mechanisms of the fixation device 100, before being implanted in the patient.

Rather than fixation device 100, any of the above fixation devices (120, 200, 300, 400, 420, or 500) may be used in similar fashion to that shown in FIGS. 8A-8C.

FIGS. 9A-9F depict an illustrative three incision method for implanting a medical device, such as the S-ICD system in a patient 900. Beginning with FIG. 9A, certain anatomy of the patient 900 is highlighted including a heart 902 and sternum 904.

A xiphoid incision 906 may be made just to the left of and superior of the xiphoid near the lower portion of the sternum 904, and an axillary incision may be made near the left axilla of the patient 900, as shown at 908.

An insertion tool 910 may be used in the procedure. The insertion tool 910 may have a handle 912 at a proximal end 918, and an elongate shaft 914 extends distally from the handle 912 toward a distal dissecting tip 920 that includes an attachment feature 916. The attachment feature 916 is shown as a suture opening, however, other suitable attachment features known in the art may be used.

The distal tip 920 may be shaped for dissection of subcutaneous tissue. In one example, the distal tip 920 has a tapered blunt tip, allowing for passage by dissection between layers of subcutaneous tissue, preferably staying within the subcutaneous fat layer for advancement, without encouraging piercing through the epidermis or an intercostal space. A channel(s) may be provided in the insertion tool 910 to allow infusion of fluids for antiseptic, anti-inflammatory, pain reduction, or other purposes at the dissecting tip or along the length thereof. If ingrowth or adhesion is desired, a tissue adhesive or steroid may be infused as well. As shown by the arrow in FIG. 9A, the insertion tool 910 may be inserted through the xiphoid incision 906 and advanced to the axillary incision 908.

Figure 9A:
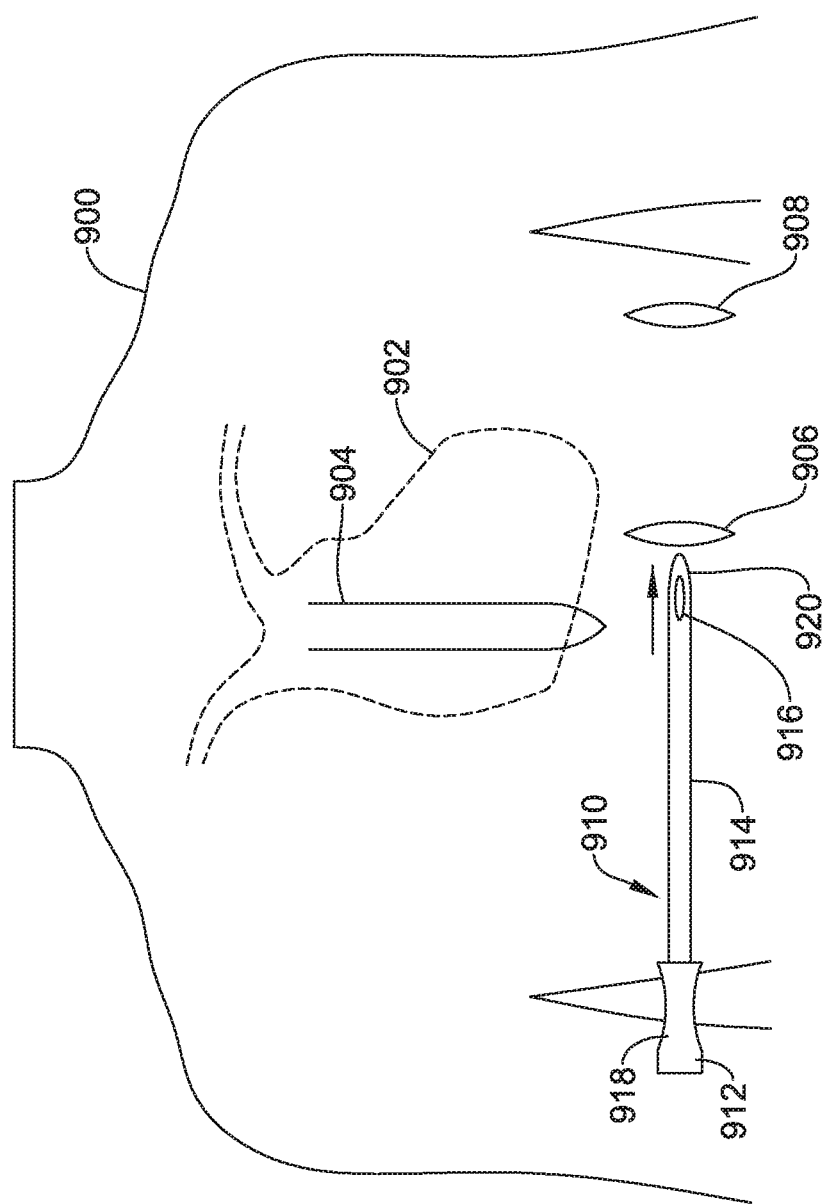
Figure 9B:
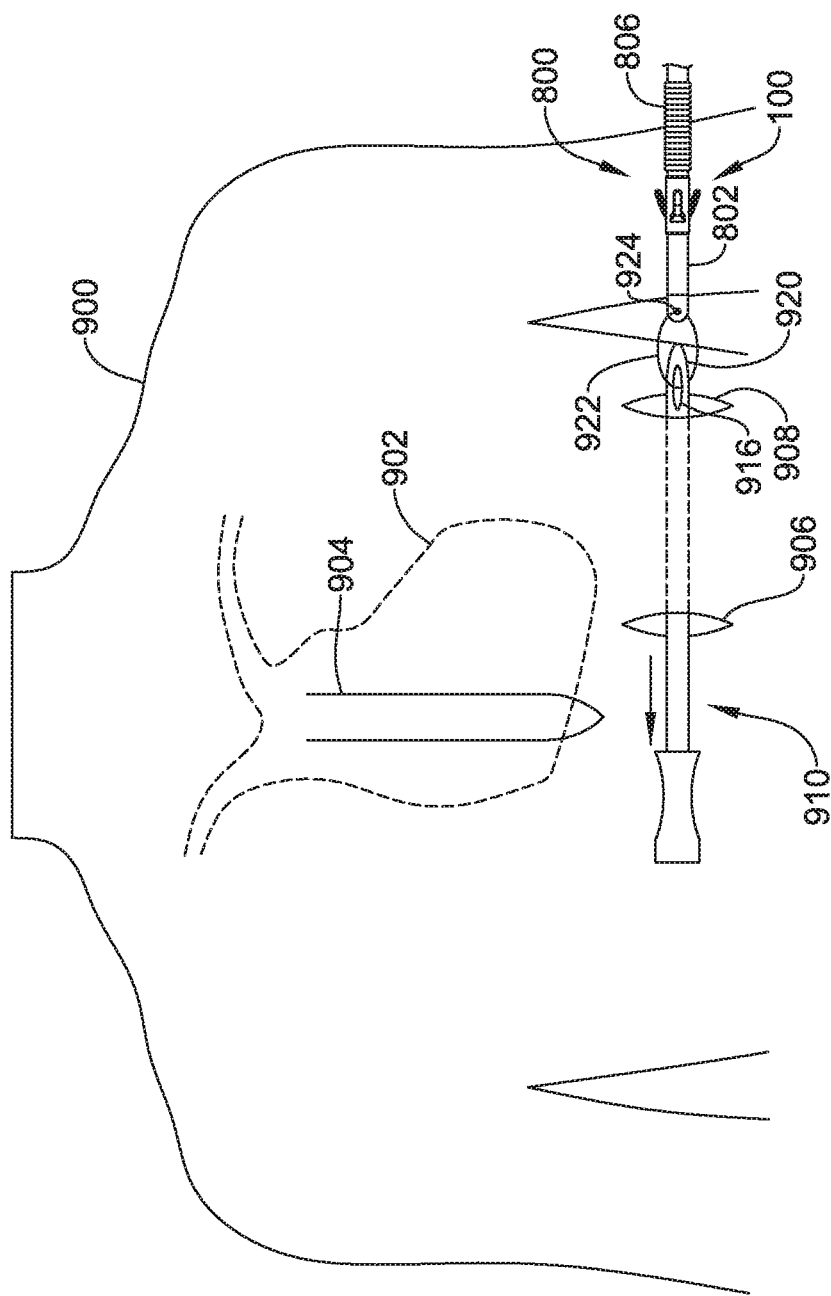

As shown in FIG. 9B, the lead 800 has previously been prepared for use with a fixation device 100 placed thereon; any of the fixation devices shown herein may be used along with a tool as shown above for such preparation. In some examples, a sheath (not shown) may be placed over the lead 800 and fixation device 100 for purposes of introduction into the patient, so as to prevent interaction of the securing mechanisms thereof with patient tissue.

The insertion tool 910 may be inserted into the xiphoid incision until its distal tip 920, including the attachment feature 916, can be accessed through the axillary incision 908. Then a suture 922 may be used to attach the attachment feature 916 of the insertion tool 910 to an attachment feature 924 on the distal tip portion 802 of the lead 800. Next, the insertion tool 910 may be withdrawn through the xiphoid incision 906, with the suture 922 pulling the lead 800 into the patient's 900 subcutaneous tissue through the axillary incision 908.

In an alternative, the lead may be pushed into the patient, alone or with a sheath thereon. For example, an introducer sheath may be used to restrain the fixation device to prevent interaction with tissue during implant, and the introducer sheath may also be used to aid in advancing the lead into the tissue tunnel from the axillary incision to the xiphoid incision. If a sheath is used in this manner, the tunneling between axillary incision and xiphoid incision may be performed in either direction (xiphoid to axillary or axillary to xiphoid), if desired. In other examples, a sheath can be applied over the lead and stays in place as it is pulled into position, without the sheath being used to aid in pushing the lead into place.

The end of this pulling step (or advancement) is shown in FIG. 9C, where the attachment feature 924 at the distal tip portion 802 of the lead 800 extends through the xiphoid incision 906. At the end of this step, a proximal plug 826 of the lead 800 may be located relatively near the axillary incision 908, though this may depend on the anatomy of the patient 900 and the length of the lead 800.

In the example shown in FIG. 9C, the suture 922 remains attached to the insertion tool 910, which is shown in alignment with the sternum 904 in preparation for the next step of the procedure. In the alternative, if the lead was pushed through the axillary/xiphoid tunnel (alone or using a sheath), a suture may be attached at this point in the procedure. An upper incision 928 may be made a short distance to the left of the sternum 904 at a location that is superior to the xiphoid incision 906, approximately along the left sternal margin. For example, the upper incision 928 may be located approximately 8 to 18 cm superior of the xiphoid incision 906, and 1-3 cm left of the sternum 904. The upper incision 928 may also be described as level with or inferior to the manubrium and/or level with or superior to the atria of the heart. These particular locations are illustrative and not required; various implant locations can be used. For example, other subcutaneous locations may be used, such as shown in U.S. Pat. Nos. 6,647,292, 6,721,597, 7,194,302, 7,149,575 and/or 7,655,014, which are incorporated herein by reference. The insertion tool 910 may then be reinserted into the xiphoid incision and advanced generally parallel to the sternum 904 toward and through the upper incision 928.

Turning to FIG. 9D, the distal tip 920 of the insertion tool 910 extends out of the upper incision 928 until the attachment feature 916 can be accessed. Next, a forceps (not shown) may be used to grasp the suture 922, which may be cut from the attachment feature 916. The insertion tool 910 may then be withdrawn.

Figure 9E:
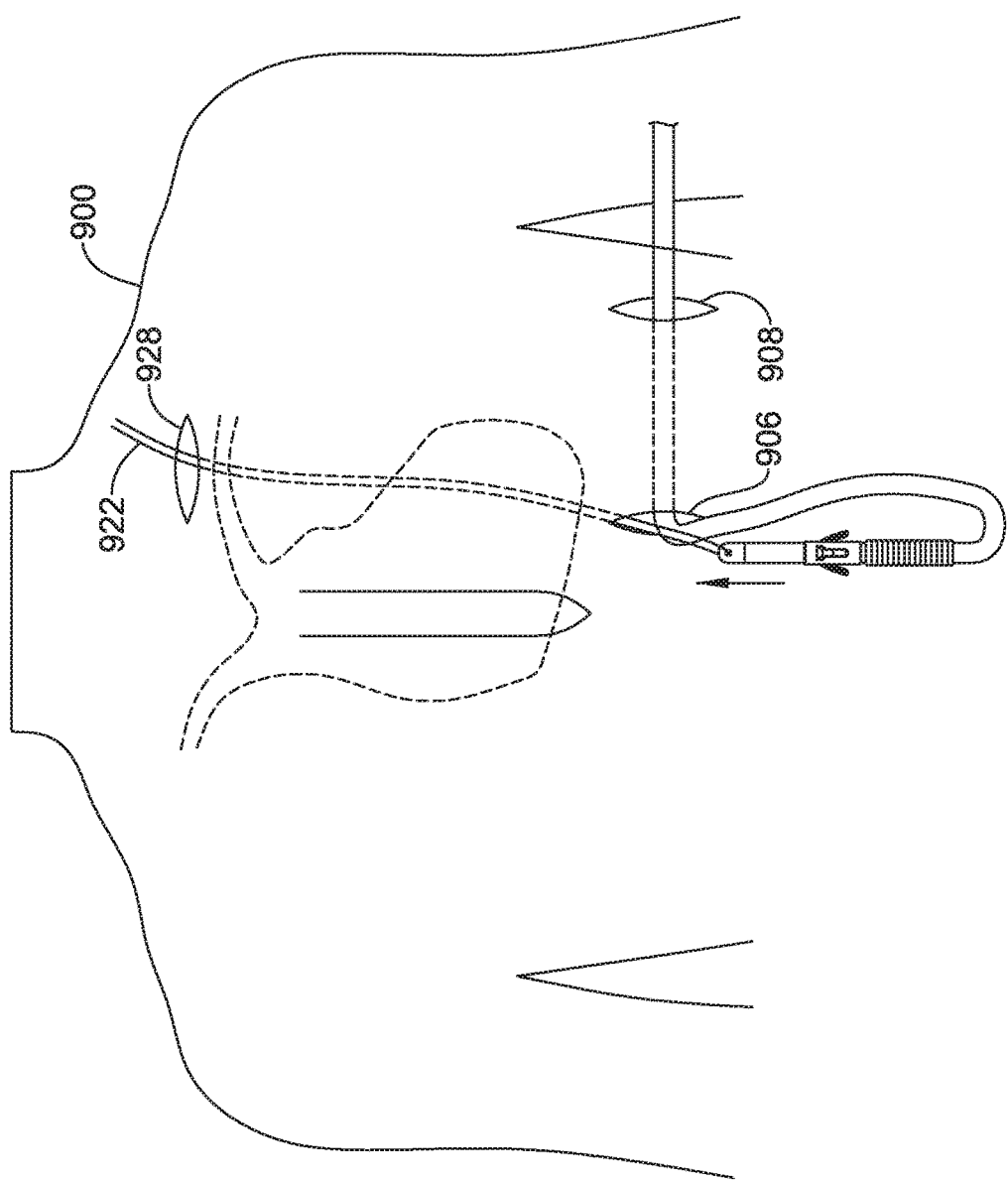
Figure 9F:
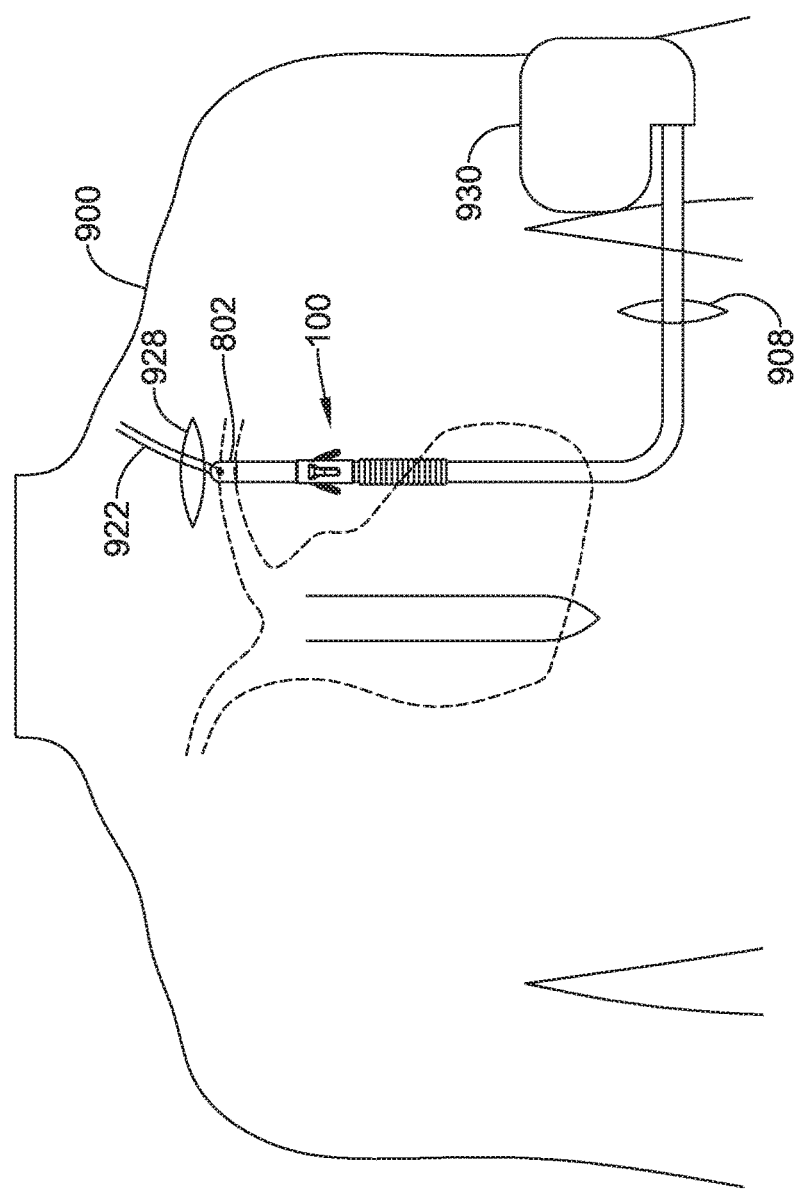

Turning to FIG. 9E, the forceps (not shown) may be used to pull the suture 922 through the upper incision 928, drawing the lead 800 through the xiphoid incision 906 into the patient 900 and through the tunnel formed by the insertion tool 910. The suture 922 may be pulled until the lead 800 achieves the position shown in FIG. 9F, where the distal tip portion 802 of the lead 800 and its attachment feature 924 are near to, or may be accessed at, the upper incision 928. The proximal plug 926 of the lead 800 may be attached to an implantable pulse generator or canister 930. The canister 930 may then be implanted through the axillary incision 908 and sutured to the patient 900 tissue.

In some examples, the method of FIGS. 8A-8C may be performed prior to or at the start of surgery, such that the fixation device 100 is applied to the lead before the lead is inserted into the patient. In an alternative example, the fixation device 100 may be applied using a tool as shown above in FIGS. 8A-8C after the lead has been advanced into the patient's tissue, such as after advancement to the upper sternal incision, which would eliminate concerns about the fixation device engaging tissue as the lead is passed through subcutaneous tissue until reaching the desired position.

Additionally, in this embodiment, the securing mechanisms 104A-104C of the fixation device 100 may engage, push against, and/or anchor the lead 800 to the patient 900 tissue (e.g. the tunnel formed by the insertion tool 910). The fixation device 100 may provide several potential benefits. For instance, the fixation device 100 may improve stability during implantation of the lead 800, with or without the use of an introducer sheath. The fixation device 100 may also improve stability during acute implant duration, prior to tissue ingrowth. In some cases, the fixation device 100 may potentially improve long term stability, including a chance for less noise due to electrode movement, for example. In some cases, the fixation device 100 may eliminate the need for suturing. Moreover, current implantation techniques may be performed with leads having the fixation device 100, with or without the use of an introducer sheath. In some cases, a physician may consider the use of the fixation device 100 in patients with a specific body habitus that is known to increase the risk of electrode movement.

Several modifications may be made to the method of implanting the subcutaneous defibrillator described in FIGS. 9A-9F. For example, several alternative structures for leads and fixation devices may be used and additional steps/features may be are provided. In one example, the fixation device may take the form of the fixation devices 120, 200, 300, 400, 420, or 500 shown above.

Figure 10A:
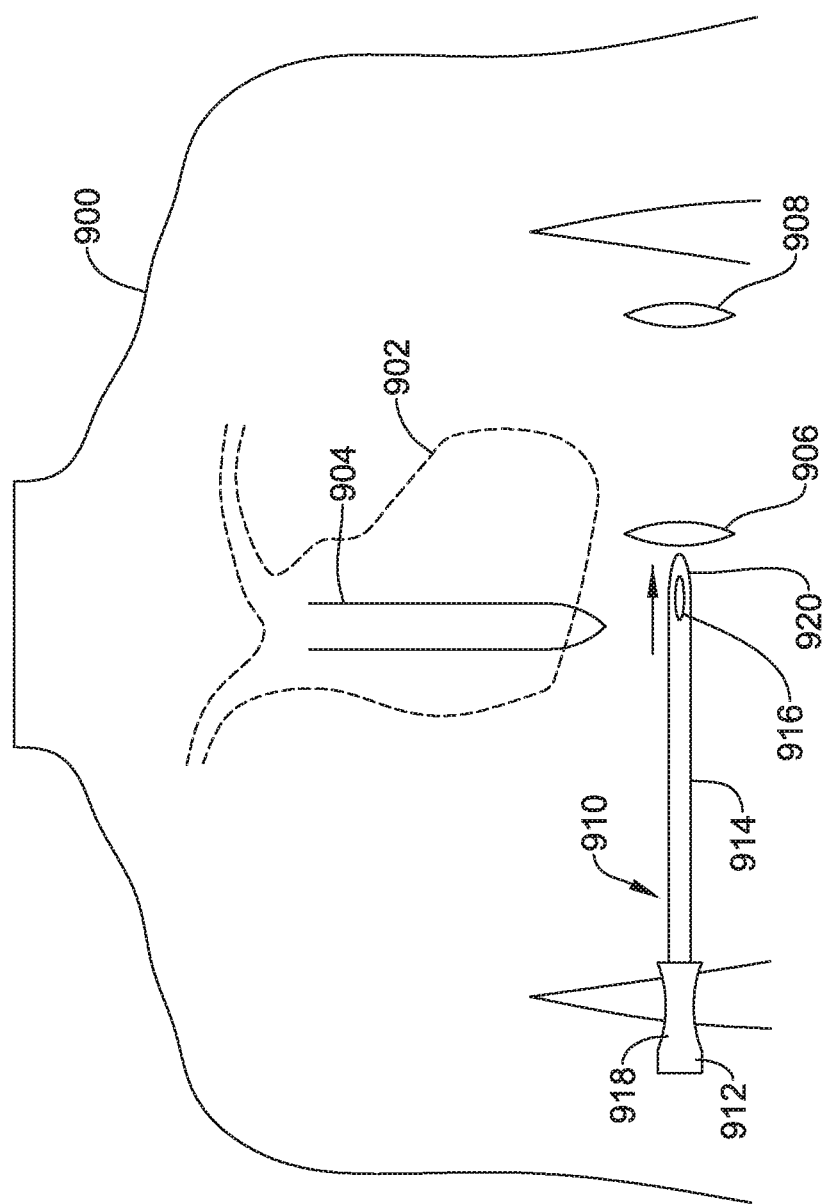

FIGS. 10A-10E depict an illustrative two incision method of implanting a medical device in the patient 900. The beginning of the two incision method may be similar to the three incision method depicted in FIGS. 9A-9B. As shown in FIG. 10A, the xiphoid incision 906 and the axillary incision 908 are made. The insertion tool 910 may then be inserted through the xiphoid incision 906 and advanced toward the axillary incision 908.

Figure 10B:
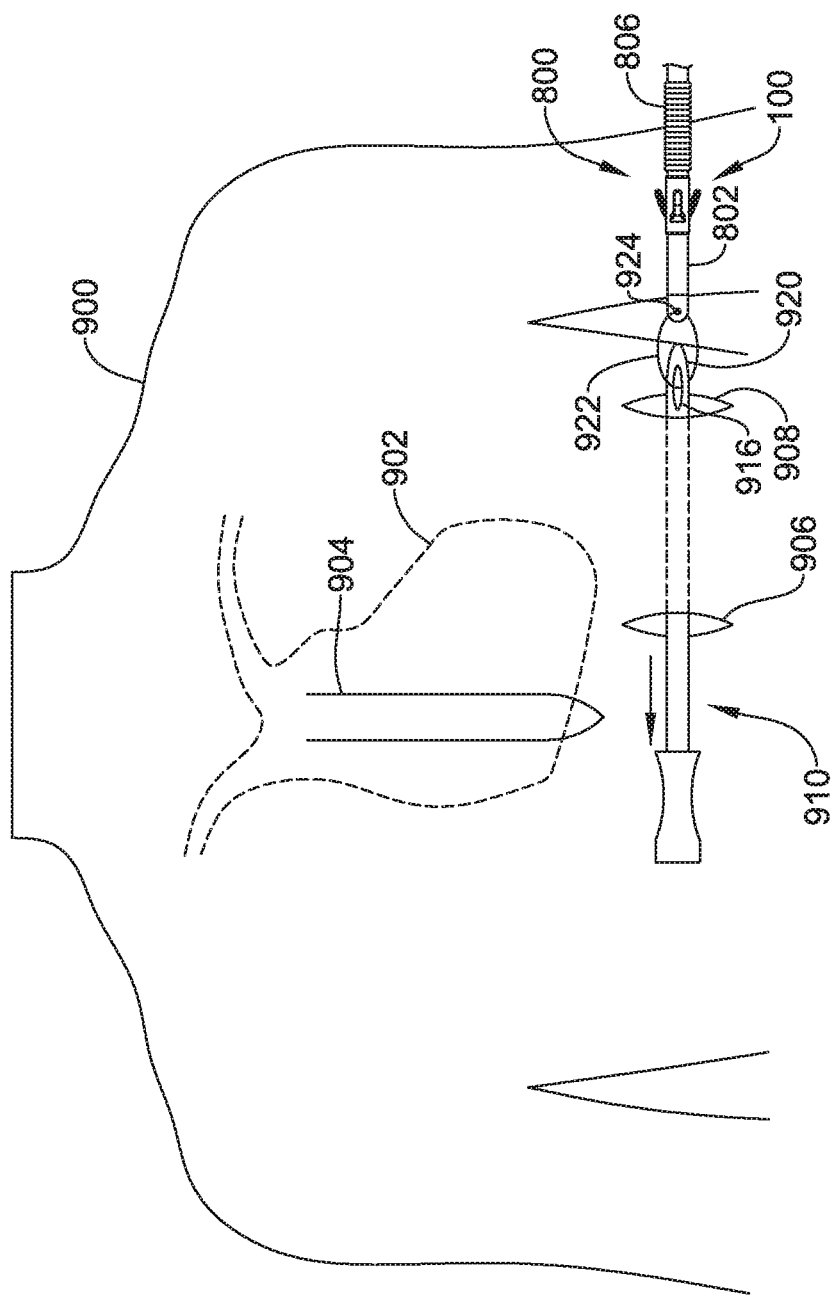

As shown in FIG. 10B, the insertion tool 910 may be inserted into the xiphoid incision 906 until its distal tip 920, including the attachment feature 916, can be accessed through the axillary incision 908. Then the suture 922 may be used to attach the attachment feature 916 of the insertion tool 910 to the attachment feature 924 on the distal tip portion 802 of the lead 800. Next, the insertion tool 910 may be withdrawn through the xiphoid incision 906, with the suture 922 pulling the lead 800 into the patient's 900 subcutaneous tissue through the axillary incision 908.

Figure 10C:
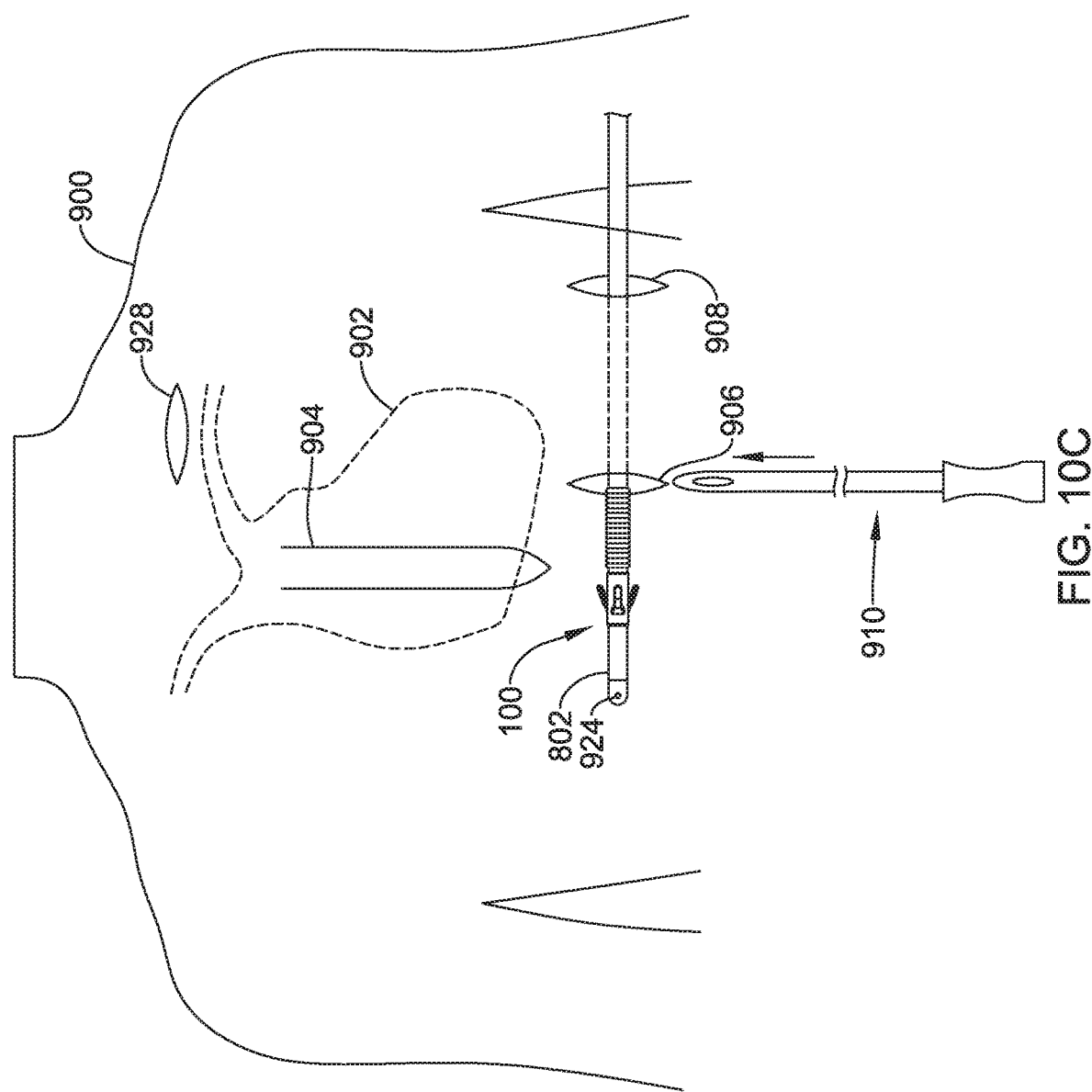

The end of this pulling step is shown in FIG. 10C, where the attachment feature 924 at the distal tip portion 802 of the lead 800 extends through the xiphoid incision 906 and forceps (not shown) may be used to grasp the suture 922, which may be cut from the attachment feature 916. At the end of this step, the proximal plug 926 of the lead 800 may be located relatively near the axillary incision 908, though this may depend on the anatomy of the patient 900 and the length of the lead 800.

In the example shown in FIG. 10C and as described herein, the distal tip 920 of the insertion tool 910 may be shaped to allow for passage by dissection through subcutaneous tissue. Accordingly, the insertion tool 910 may be reinserted into the xiphoid incision 906 and advanced generally parallel to the sternum 904 to create a tunnel 1000, as shown in FIG. 10D. The insertion tool 910 may then be withdrawn. The insertion tool may have an insertion sheath thereon during at least the tunneling step of FIG. 10C (it may also be present during the tunneling step of FIG. 10A). Once the tunnel 1000 is made, the insertion sheath may be held in place as the insertion tool 910 is removed.

Figure 10E:
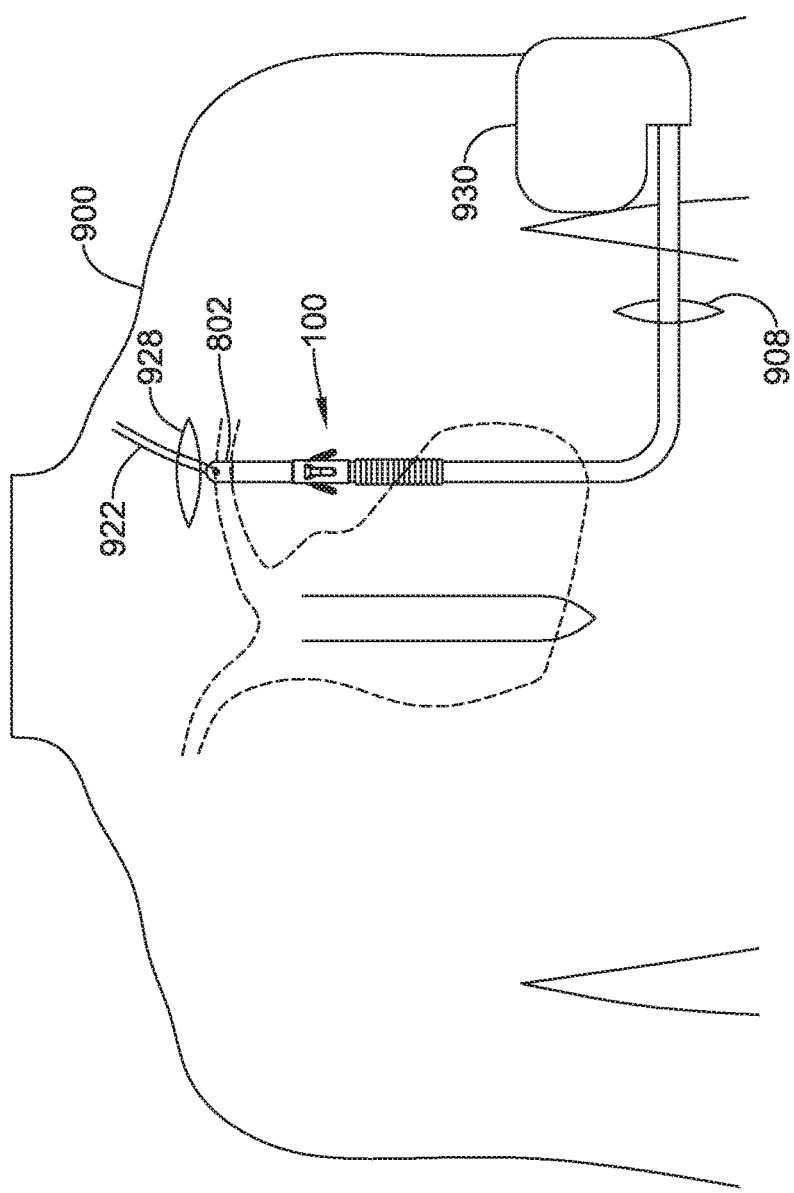

As shown in FIG. 10E, the lead 800 may be inserted into the xiphoid incision 906 through the splittable sheath, and advanced generally through the tunnel 1000. The splittable sheath can then be removed, releasing the securing mechanisms of the fixation device 100 to engage the tissue and hold the lead in place. The proximal plug 926 of the lead 800 may then be attached to the canister 930 and the canister 930 may be implanted through the axillary incision 908 and sutured to the patient 900 tissue. If desired, a suture sleeve may be attached at the xiphoid incision for further securing the lead 800 in place.

As with the three incision method, fixation device 100 may be placed on the lead prior to the start of the procedure, or may be applied in the middle of the procedure such as after the axillary-to-xiphoid tunnel is traversed by the lead 800. It may be noted that, except for use of the fixation device, much of the discussion of the two incision method may make use of concepts similar to that shown in U.S. Pat. No. 7,655,014, titled APPARATUS AND METHOD FOR SUBCUTANEOUS ELECTRODE INSERTION, the disclosure of which is incorporated herein by reference. Likewise, the three incision method may be similar to that contained in the approved instructions for use from PMA P110042, covering the S-ICD System.

Figure 11A:
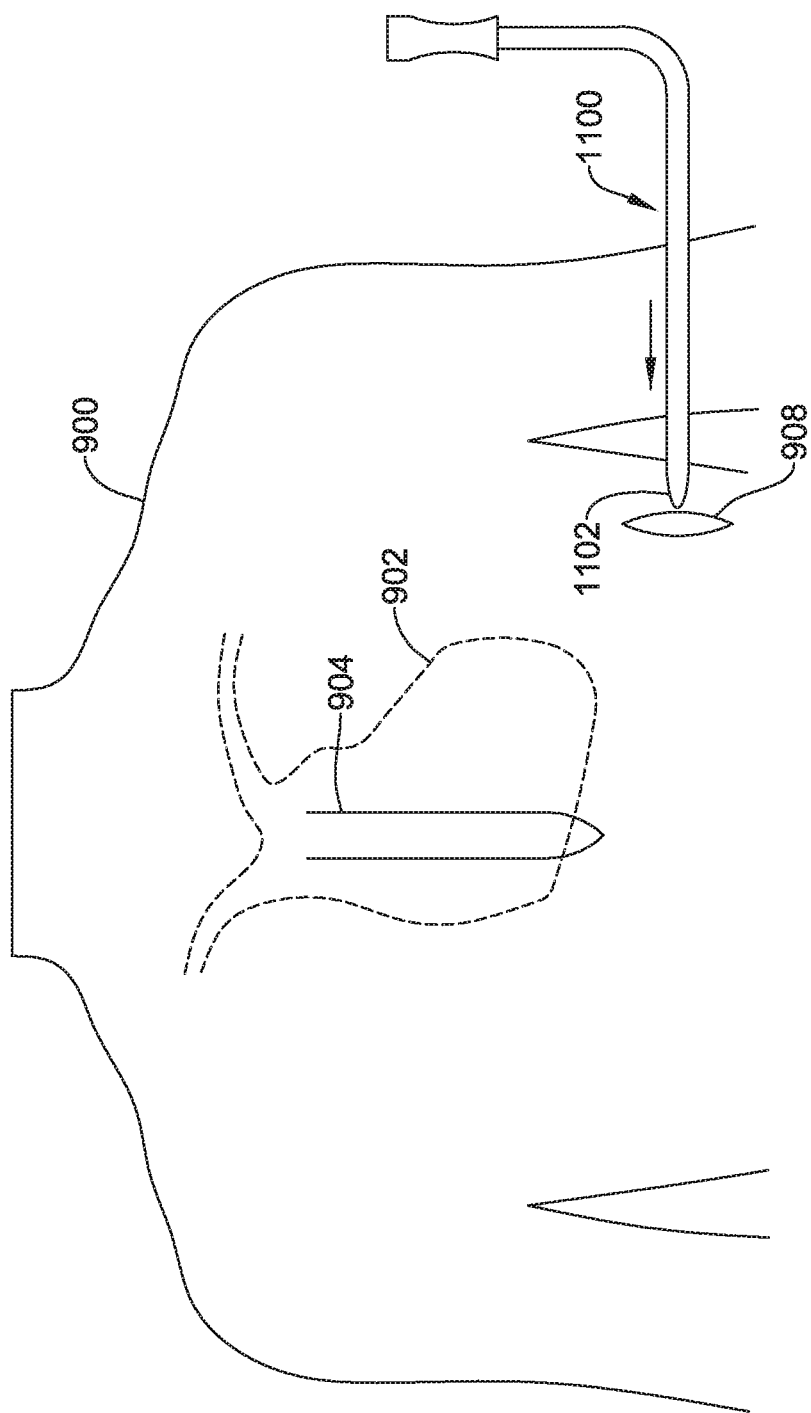
FIGS. 11A-11C show a single incision method for implanting a lead.
Figure 11B:
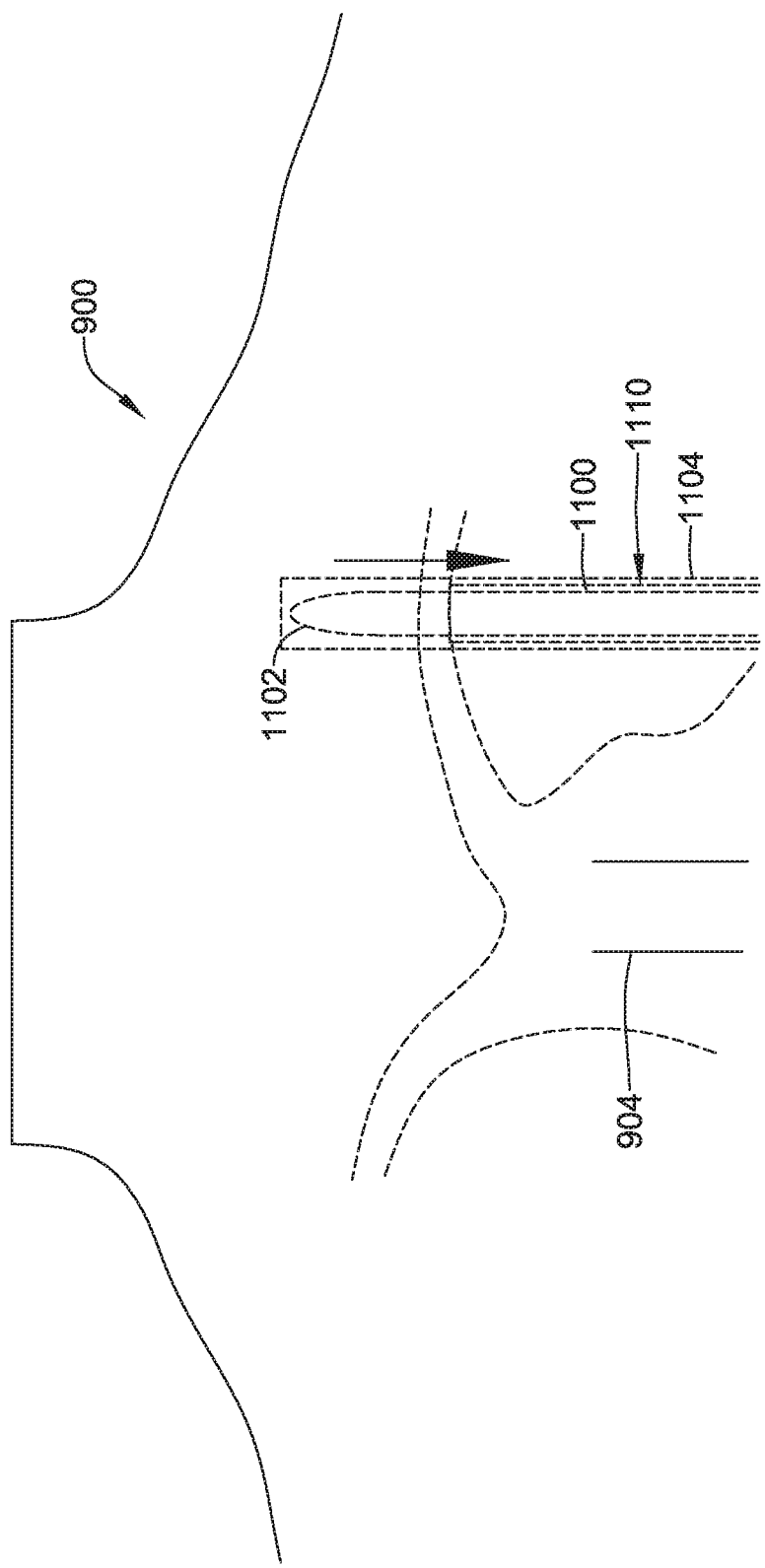
Figure 11C:
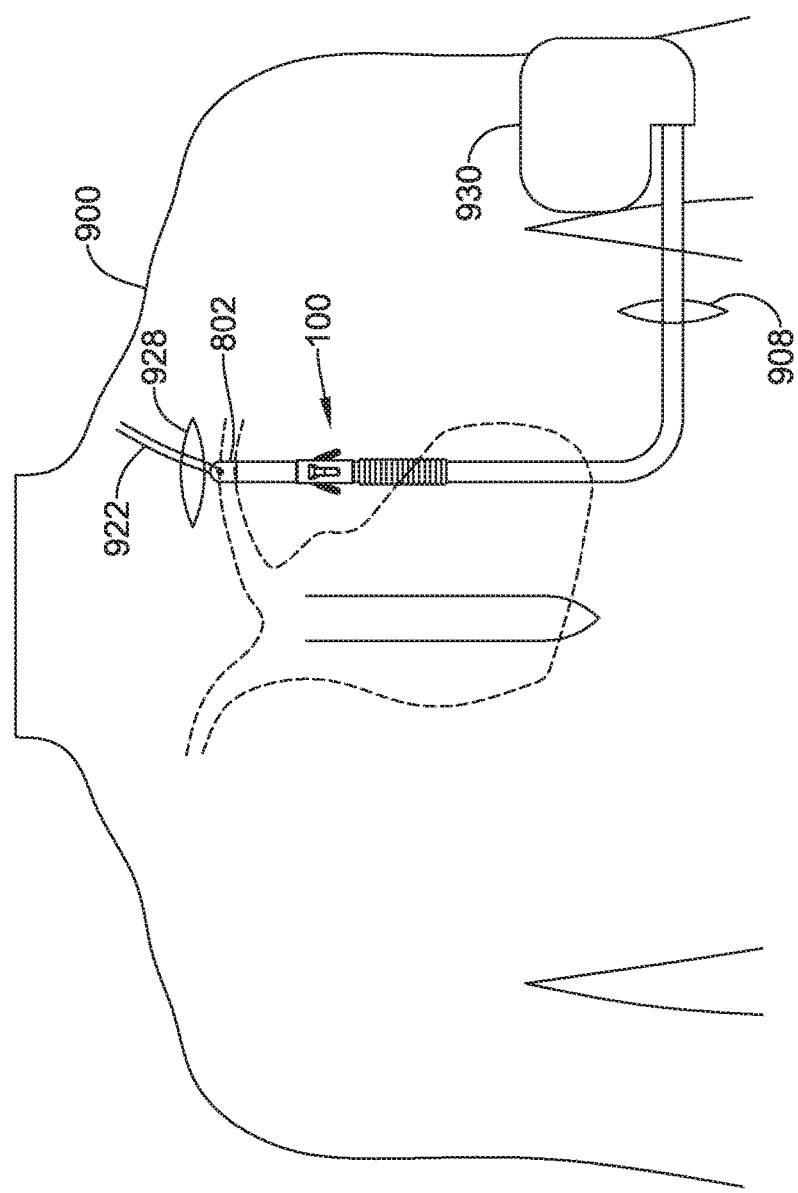

FIGS. 11A-11D depict an illustrative one incision method of implanting a medical device in the patient 900. As shown in FIG. 11A, the axillary incision 908 is made and a curved insertion tool 1100 may be inserted through the axillary incision 908. A splittable sheath 1110 is placed over the insertion tool 1100. The insertion tool 1100 may be similar to the insertion tool 910 (from FIGS. 9A-9D and 10A-10D) in that the insertion tool 1100 may also have a distal tip 1102 that is shaped to allow for passage by dissection through subcutaneous tissue. The tool shown may be malleable to a shape selected for a given patient, as suggested in U.S. Pat. No. 7,655,014, the disclosure of which is incorporated herein by reference. Alternatively, the insertion tool 1100 may be deflectable or steerable and may be used to create a tunnel 1104 from the axillary incision 908, just to the left of and superior of the xiphoid near the lower portion of the sternum 904, and advanced generally parallel to the sternum 904, as shown in FIG. 11B.

For example, a tool set as shown in US PG Patent Application Publication No. 20170020551 may be used, with a splittable sheath 1110 placed over the tool used to create the final tunnel shape. The disclosure of the 20170020551 publication is incorporated herein by reference. The insertion tool 1100 may then be withdrawn, while the splittable sheath is held in place. In another example, a single incision method may also or instead use a method as shown in U.S. Provisional Patent Application No. 62/546,832, titled SINGLE INCISION SUBCUTANEOUS IMPLANTABLE DEFIBRILLATION SYSTEM, the disclosure of which is incorporated herein by reference. Using the method of the copending provisional application, the insertion tool may be used to place a splittable sheath along a desired implantation path.

The lead is then inserted through the splittable sheath 1110. As the lead is introduced, the sheath 1110 constrains the securing mechanisms of the fixation device 100 until a desired position is achieved. Once the desired position is achieved, the splittable sheath is removed, allowing the securing mechanisms of the fixation device 100 to engage surrounding tissue to hold the lead in place. As shown in FIG. 11D, the lead 800 and particularly the distal end thereof 802 may be positioned at a desired location in the tunnel 1104. The proximal plug 926 of the lead 800 may then be attached to the canister 930 and the canister 930 may be implanted through the axillary incision 908 and sutured to the patient 900 tissue.

As shown above, three general implantation methods are shown. Various alternatives to steps and devices shown are identified. At a high level, a three incision technique is shown with a sternal incision, a xiphoid incision, and an axillary incision, wherein a lead having an fixation device either preloaded or applied intraoperatively is placed. The fixation device may then be used to eliminate the suturing steps used in prior implementations of the S-ICD System at the distal tip/upper sternal incision, potentially reducing procedure time and reducing the likelihood of migration which may occur due to suture disintegration or due to sutures untying, the former of which is more likely with natural and particularly dissolvable sutures, and the latter of which is more likely with synthetic and lubricious sutures.

At a high level, a two incision technique is shown that omits the upper sternal incision of the three incision technique; a sheath is used to secure the parasternal tunnel and may additionally serve to support lead passage and/or to restrain or retain securing mechanisms on the lead. In the two incision technique, the present invention offers a distal tip anchor that reduces the risk of lead migration.

At a high level, a single incision method may omit each of the xiphoid and sternal incisions; a sheath is used to secure the parasternal tunnel and may additionally serve to support lead passage and/or to restrain or retain securing mechanisms on the lead. The present invention offers a distal tip anchor that reduces the risk of lead migration.

In each of the three implant methods, the present invention allows additional anchoring at or near the distal tip of a lead without necessarily requiring that existing leads be modified for the purpose. Thus a physician may have the flexibility of using a conventional S-ICD System lead for a traditional two or three incision technique, with a fixation mechanism as shown available to provide additional or alternative anchoring options.

Figure 12:
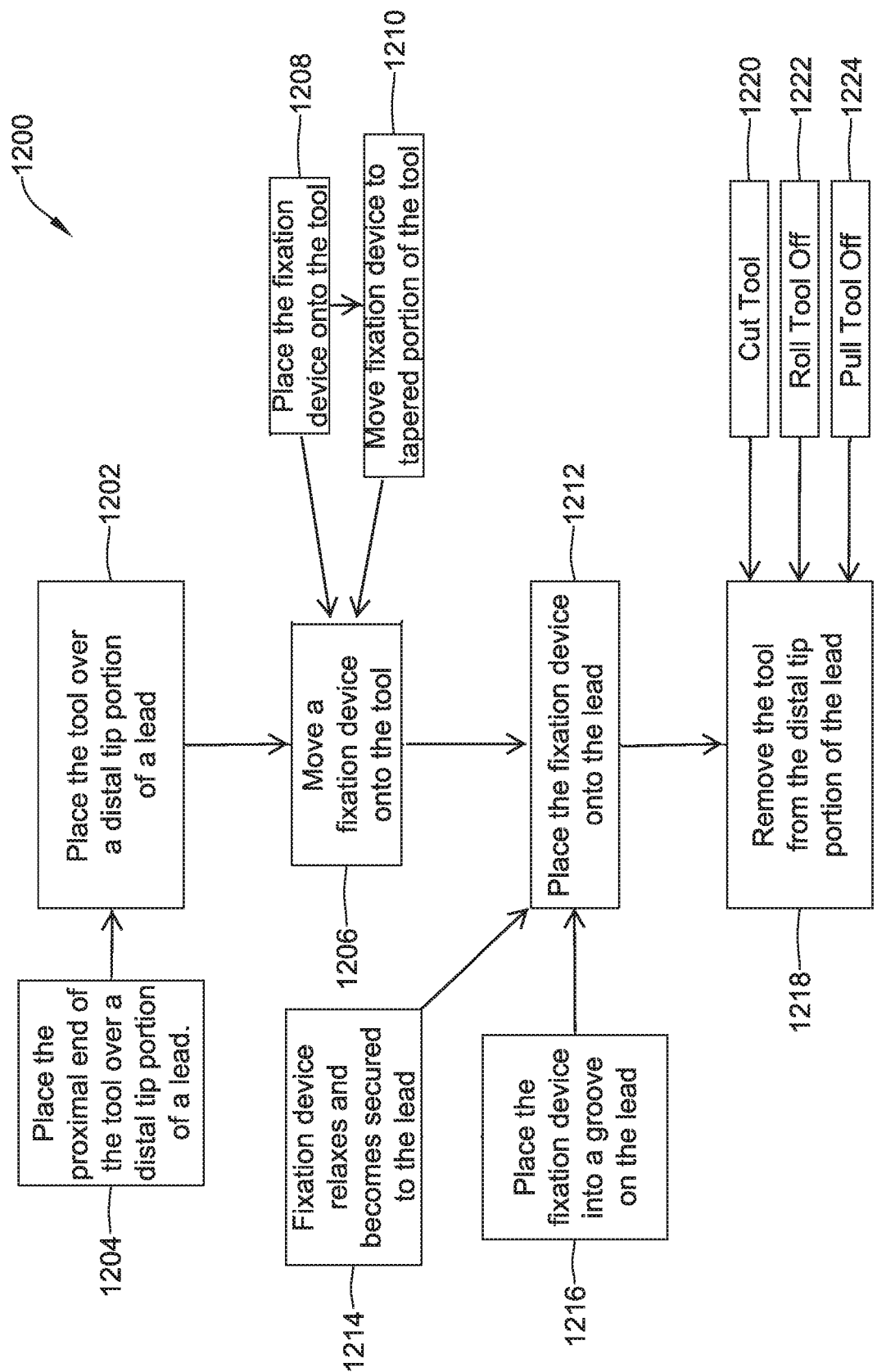
FIG. 12 is a block flow diagram for an illustrative method.

FIG. 12 is a block flow diagram for an illustrative method of preparing a lead for implantation in a patient 1200. As shown at 1200, the method comprises placing a tool over a lead 1202, moving a fixation device onto the tool 1206, placing the fixation device onto the lead 1212, and removing the tool from the lead 1218.

For example, placing the tool on the lead 1202 may include stretching a proximal end of the tool that may be formed of a suitable flexible material, over a distal tip portion of the lead 1202. Alternatively, the tool may be sized to receive the distal tip of the lead 1202 without stretching. Accordingly, a cavity of the tool may receive the distal tip portion and as a result, the tool may be coupled to the lead. Thus as indicated at 1204, a proximal end portion of a tool can be placed over the distal tip of the lead.

In an example, moving the fixation device onto the tool 1206 may include the fixation device fitting around and being placed onto the tool 1208. In some examples, an outer diameter near a distal end of the tool may be smaller than an inner diameter of the fixation device. This may allow the fixation device to fit around and be placed onto the tool. In some examples, silicone oil or other lubricant may be applied to the inner diameter of the fixation device during manufacturing to facilitate ease of placement and movement of the fixation device on the tool. In an example, the fixation device may then be moved along the tool until it reaches a tapered portion of the tool 1210. In some examples, the tapered portion may have an outer diameter that is initially smaller than the inner diameter at a proximal end of the fixation device. However, as the fixation device moves along the tapered portion, the outer diameter may become greater than the inner diameter of the fixation device. In some examples, a body of the fixation device may be comprised of a flexible material. In an example, as the fixation device moves along the tapered portion, the body may be stretched and moved from the tapered portion, to the proximal end of the tool.

In an example, placing the fixation mechanisms onto the lead 1212 may include sliding the fixation device off of the tool and onto the lead. The fixation device can then become fixed on the lead. In one example, the fixation device relaxes to a smaller inner diameter, as indicated at 1212, where the relaxed fixation device inner diameter is less than the outer diameter of a portion of the lead where it is placed, creating a friction fit therebetween to hold the fixation device in position. In an example, placing the fixation mechanism onto the lead 1212 may include placing the fixation mechanism into a groove on the lead 1216. In some examples, the groove may be configured to receive and hold or impede the fixation device from moving farther down the lead and onto an electrode included on the lead. In some examples, the groove may also hold or impede the fixation device from moving back onto the distal tip portion of the lead and potentially off the lead.

In various examples, removing the fixation device from the lead 1218 may include cutting the proximal end of the tool 1220, rolling the proximal end of the tool 1222 off of the distal tip portion of the lead, or pulling the tool in the opposite direction of the lead 1224. Once the tool has been removed, the lead may be ready for implantation into the patient or ready for further preparation necessary before being implanted in the patient.

Some embodiments of the present invention may take the form of an implantation tool set configured for use in implanting a medical device, such as a lead. Some such embodiments may include an insertion tool for dissecting a subcutaneous path, an introducer sheath that may be placed over a lead or over the insertion tool, a tool for applying a fixation device to a lead, and a fixation device for placement on a lead to allow fixation of the lead in a patient. While the present invention may generally be used in any location of the body to anchor a lead, some examples shown are specific to fixation of a lead to a subcutaneous location.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

Any suitable lead structure may be used, such as leads adapted for subcutaneous implantation for cardiac monitoring or therapy purposes, and/or leads adapted for use in spinal, deep brain, or peripheral neuromodulation systems such as vagus or sacral nerve therapies.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of preparing a lead for implantation in a patient, the method using:
   a lead having a proximal end adapted for coupling to an implantable medical device, and a distal end having a distal tip;
   a fixation device having a body with a lumen therethrough and at least one securing mechanism integral with or attached to the body; and
   a tool for fixation device placement, the tool having a proximal end with a cavity adapted to receive the distal end of the lead, a distal end sized to fit within at least a portion of the lumen of the fixation device and a medial portion between the tool proximal and distal ends, wherein an outer surface of the fixation device is tapered between the medial portion and the proximal end such that the proximal end has a larger outer diameter than the medial portion;
   the method comprising:
   placing the distal tip of the lead into the cavity of the tool; and
   sliding the fixation device from the medial portion of the tool toward and over the proximal end of the tool and onto the lead;
   wherein during the sliding step the inner diameter of the fixation device lumen is expanded by the tapered outer surface of the tool.

2. The method of claim 1, further comprising removing the tool from the distal tip of the lead.

3. The method of claim 1, wherein the proximal end of the tool is comprised of a flexible material configured to stretch over the distal tip of the lead allowing the cavity to receive the distal tip portion of the lead.

4. The method of claim 1, wherein the body of the fixation device is comprised of a flexible material configured to stretch, allowing the fixation device to move over the tool and the distal tip portion of the lead.

5. The method of claim 1, wherein a portion of the lead includes a groove or depression configured to receive the fixation device and hold the fixation device in place on the lead.

6. The method of claim 1, wherein the at least one securing mechanism of the fixation device has a first end coupled to the body and a second end adapted to extend away from the body, wherein the at least one securing mechanism is configured for both a collapsed position for use during implantation and an extended position to impede movement relative to patient tissue, and the method further comprises placing a sheath over a portion of the lead including the fixation device to constrain the at least one securing mechanism in the collapsed configuration for implant.

7. The method of claim 6, wherein the at least one securing mechanism includes a first securing mechanism and a second securing mechanism and the first securing mechanism has a first degree of angular separation with the body that is substantially equal to a second degree of angular separation of the second securing mechanism with the body.

8. The method of claim 6, wherein the at least one securing mechanism includes a shape memory metal material therein and, when the sheath is placed on the at least one securing mechanism, the shape memory metal can be readily collapsed, while once in the body of the patient during insertion of the device, the shape memory metal exerts force to adopt the extended position.

9. A method of implanting a lead in a patient comprising: performing a method as in claim 1 to prepare the lead for implantation in the patient by placing the fixation device on the lead; and advancing the lead and the fixation device through an incision and to a desired location in the patient.

10. The method of claim 9 further comprising
- prior to advancing the lead and the fixation device to the desired location in the patient, placing a sheath over the lead after the fixation device is placed on the lead, such that the sheath constrains the at least one securing mechanism of the fixation device; and
- after advancing the lead and the fixation device to the desired location in the patient, removing the sheath to release the at least one securing mechanism of the fixation device.

* * * * *